United States Patent
Schoenafinger et al.

(10) Patent No.: US 7,879,864 B2
(45) Date of Patent: Feb. 1, 2011

(54) SUBSTITUTED 8-AMINOALKOXY-XANTHINE COMPOUNDS AND COMPOSITIONS USEFUL IN THE TREATMENT OF HYPERLIPIDEMIA AND DIABETES

(75) Inventors: Karl Schoenafinger, Alzenau (DE); Gerhard Jaehne, Frankfurt (DE); Elisabeth Defossa, Idstein (DE); Christian Buning, Bonn (DE); Georg Tschank, Essenheim (DE); Ulrich Werner, Miehlen (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 663 days.

(21) Appl. No.: 11/674,261

(22) Filed: Feb. 13, 2007

(65) Prior Publication Data
US 2007/0299090 A1    Dec. 27, 2007

Related U.S. Application Data

(63) Continuation of application No. PCT/EP2005/008283, filed on Jul. 30, 2005.

(30) Foreign Application Priority Data
Aug. 14, 2004    (DE)    ........................ 10 2004 039 507

(51) Int. Cl.
C07D 473/02    (2006.01)
A61K 31/522    (2006.01)
A61P 3/10    (2006.01)
A61P 3/06    (2006.01)

(52) U.S. Cl. .................. 514/263.2; 514/263.22; 514/263.31; 514/263.32; 514/263.33

(58) Field of Classification Search .............. 514/263.2, 514/263.22, 63.31, 263.32, 263.33; 544/266
See application file for complete search history.

(56) References Cited

U.S. PATENT DOCUMENTS

| | | | |
|---|---|---|---|
| 2,688,618 A | | 9/1954 | Cooper, et. al. |
| 4,742,065 A | * | 5/1988 | Klosa et al. ................. 544/266 |
| 5,290,801 A | | 3/1994 | Higley et al. |
| 6,143,743 A | | 11/2000 | Wilde et al. |
| 2007/0265284 A1 | * | 11/2007 | Schoenafinger et al. .. 514/263.3 |
| 2009/0018148 A1 | | 1/2009 | Moureau et al. |
| 2009/0163545 A1 | | 6/2009 | Goldfarb |

FOREIGN PATENT DOCUMENTS

| DE | 1005517 | * | 4/1957 |
|---|---|---|---|
| EP | 0430300 | | 11/1990 |
| WO | WO 92/05175 | | 4/1992 |
| WO | WO 0063208 | | 10/2000 |
| WO | WO 02068420 | | 9/2002 |
| WO | WO 2004/048379 | | 6/2004 |

OTHER PUBLICATIONS

Kejha, J., et. al., Iodinated Phenoxyalkyltheophyllines, Cesko-Slovenska Farmacie (1966), vol. 15, No. 1, pp. 2-4.
Truta, E., et. al., The Effects Induced by 8-(4-R)-Phenoxymethylxanthinic Compounds on Germination, Plantlet Growth and Mitosis in Allium Cept L, Analele Stiintifice Ale Universitatii Al. I. Cuza Din Iasi, Sectiunea 2A: Genetica Si Biologie Moieculara Bd. 2001, Nr. 1, Seiten 43-49XP002361403 Chemical Abstracts Service.
Blandine Laferrere et al., Effects of bombesin, of a new bombesin agonist (BIM187) and a new antagonist (BIM189) on food intake in rats, in relation to cholecystokinin, European Journal of Pharmacology, (1992), vol. 215(1), pp. 23-28.
Corri Black et al., Meglitinide analogues for type 2 diabetes melitus, The Cochrane Collaboration Review, (2007).
Krutovskikh, G. N., et al, Radioprotective Properties of Mercaoticaffeine Derivatives, Khimiko-Farmatsevticheskii Zhumal (1975), vol. 9(4), pp. 21-23, (Abstract Only).
Renzo Cescato et al., Bombesin Receptor Antagonists May Be Prefereable to Agonists for Tumor Targeting, The Journal of Nuclear Medicine, (2008), vol. 49(2), pp. 318-326.
1H-Purine-2, 6-Dione, 3,7-Dihydro-1, 3-Dimethyl-7-(Phenylmethyl)-8—[(2-(1-Pipenidinyl) Ethyl]Thio]=(9Cl) (CA Index Name), Chemical Abstracts Service Database Chemabs Online! XP002348284 (2001-2002).

\* cited by examiner

*Primary Examiner*—Mark L Berch
(74) *Attorney, Agent, or Firm*—Serena Farquharson-Torres, Esq.; Scully, Scott, Murphy & Presser, P.C.

(57) ABSTRACT

Compounds for the treatment of elevated blood glucose levels and the physiological and metabolic disorders arising therefrom are disclosed which are inhibitors of the enzyme dipeptidyl peptidase IV (DDP-IV) and comprise novel substituted bicyclic 8-pyrrolidinoxanthines of formula I and their derivatives:

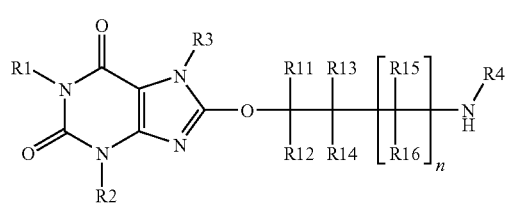

wherein the various R-groups are defined herein. These compounds may be combined with other secondary active compounds which also are effective in the treatment of said disorders and the disease states or physiological manifestations arising therefrom.

8 Claims, No Drawings

SUBSTITUTED 8-AMINOALKOXY-XANTHINE COMPOUNDS AND COMPOSITIONS USEFUL IN THE TREATMENT OF HYPERLIPIDEMIA AND DIABETES

CROSS-REFERENCE TO RELATED APPLICATIONS

This application is a continuation of International Patent Application No. PCT/EP2005/008283 filed on Jul. 30, 2005 which is incorporated herein by reference in its entirety which also claims the benefit of priority of German Patent Application No. 10/2004 039507.1 filed on Aug. 14, 2004.

FIELD OF THE INVENTION

The invention relates generally to compounds and compositions for the treatment of metabolic disorders and more particularly, those insulin-related metabolic disorders of the blood such as high blood-glucose levels, hyperlipidemia, diabetes and the like. More specifically, the present invention relates to compounds that therapeutically modulate and control lipid and/or carbohydrate metabolism and are thus suitable for the prevention and/or treatment of diseases such as type-2 diabetes and atherosclerosis, and the diverse manifestations thereof. Even more specifically, the present invention relates to 8-aminoalkoxy-xanthines, their pharmaceutically acceptable salts and functional derivatives thereof, that inhibit the activity of dipeptidyl peptidase IV (DPP-IV) and are thus very suitable for lowering the blood glucose level as therapeutic blood sugar-lowering agents among others as well as methods for their preparation and formulation as pharmaceutical compositions for the treatment of said disorders.

BACKGROUND OF THE INVENTION

Compounds comprising structures similar to the 8-aminoalkoxy-xanthine derivatives and their salts as described herein are known and have also been described in the art for the treatment of hyperlipidemia and diabetes. Basic substituted caffeine derivatives of similar structure are described in U.S. Pat. No. 2,688,618. WO92/05175 describes compounds of similar structure for the treatment of allergies.

The 8-aminoalkoxy-xanthine derivative compounds of the present invention are highly effective in the therapeutic modulation of lipid and/or carbohydrate metabolism and are therefore useful in the prevention and/or treatment of diseases such as type-2 diabetes and atherosclerosis, and the many other diverse cardiovascular, among others, manifestations arising therefrom. The utilization of an oxadiazolone feature as inhibitors of factor Xa were disclosed in DE 101 12 768 A1 and oxodiazolones have also been described as oral hypoglycemic agents in WO 96/13264.

The enzyme dipeptidyl peptidase-IV (DPP-IV) inactivates a variety of bioactive peptides, including glucagon-like peptide-1 (GLP-1) and growth hormone releasing hormone (GHRH). Inhibiting DPP-IV in order to increase circulating GLP-1 is of interest as a treatment for Type II diabetes. Inactivation of DPP-IV may also increase circulating GHRH, potentially enhancing growth in domestic animals One such substituted 8-aminoalkoxy-xanthine derivative compound similar to those of the present invention has been shown to act on the central nervous system (J. Med. Chem. (1966), 9 500-6). Inhibition of DPP-IV increases the circulating half-life of the incretin hormones GLP-1 and GIP, improving glucose tolerance in Type II diabetics. Complete inhibition of DPP-IV does not appear to be necessary as 2- to 3-fold increases in plasma concentrations of GLP-1 have been achieved in mice with inactivation of 84% to 96% of plasma DPP-IV. Thus, there has been much interest in developing DPP-IV inhibitors for the treatment of Type II diabetes and other metabolic disorders.

DPP-IV exists as both a membrane-spanning form present in cells throughout the body and a soluble circulating form. Both forms of DPP-IV have identical enzymatic activity and cleave a wide range of bioactive peptides in vitro, including hormones, neuropeptides, and chemokines. One potential regulatory role of DPP-IV is the inactivation of GHRH through cleavage of the active form, GHRH(1-44)-NH$_2$, to the N-terminally shortened inactive form, GHRH(3-44)-NH$_2$, While trypsin-like degradation of GHRH also occurs, in vitro studies using GHRH analogs designed to resist cleavage at the N-terminus have demonstrated that the primary degradation of GHRH is via DPP-IV. Substitution of Ala2 with Dali prevents DPP-IV proteolysis and administration of this analog increases GH release in swine up to 2-fold. The His1, Val2 analog of GHRH is also not degraded by DPP-IV in vitro, and it demonstrates increased plasma stability over native GHRH. GHRH analogs containing the His1, Val2 substitutions were 5.4- to 12.5-fold more potent than native GHRH in release of GH in swine. Thus, inhibition of DPP-IV in vivo may increase endogenous concentrations of GHRH and enhance GH secretion.

Compounds of similar structure have been described in the prior art such as the bicyclic xanthine derivatives and their use as DDPIV inhibitors described in U.S. Pat. No. 7,074,798 to Yoshikawa et. al. which is hereby incorporated by reference The present invention involves 8-aminoalkoxy-xanthine derivative compounds of formula I

SUMMARY OF THE INVENTION

The present invention comprises compounds and compositions for the treatment of metabolic disorders and more particularly, those insulin-related metabolic disorders of the blood such as high blood glucose levels, hyperlipidemia, diabetes, insulin-resistence and the like comprising 8-aminoalkoxy xanthines derivatives and their salts of formula I

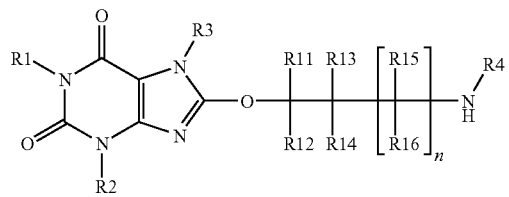

wherein the various substituent R-groups and other variables are more specifically defined herein.

DETAILED DESCRIPTION OF THE INVENTION

The present invention comprises compounds and compositions for the treatment of metabolic disorders and more particularly, those insulin-related metabolic disorders of the blood such as hyperlipidemia and diabetes and the like comprising 8-aminoalkoxy xanthine derivatives and their pharmaceutically acceptable salts of Formula I.

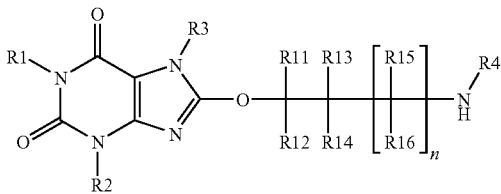

wherein:
R1, R2 and R3 are independently selected from the group consisting of H, $(C_1-C_{10})$-alkyl, $(C_3-C_{10})$-cycloalkyl, $(C_2-C_{10})$-alkenyl, $(C_2-C_{10})$-alkynyl, $(C_6-C_{10})$-aryl, heterocycle, where the alkyl, cycloalkyl, alkenyl, alkynyl, aryl and heterocycle substituents may be substituted one or more times by F, Cl, Br, I, CN, $NO_2$, $SF_5$, OH, $(C_1-C_6)$-alkyl, $-CF_3$, $-OCF_3$, $-SCF_3$, $(C_2-C_6)$-alkenyl, $(C_2-C_6)$-alkynyl, OR7, OP(O)(OR7)$_2$, NR7R8, NR7CONR7R8, COR7, OCOR7, OCOOR7, COOR7, CONR7R8, OCONR7R8, $(C_1-C_6)$-alkylene-OR7, $(C_1-C_6)$-alkylene-NR7R8, $(C_1-C_6)$-alkylene-NR7SO$_2$R7, $(C_1-C_6)$-alkylene-SR7, alkylene-S(O)R7, alkylene-CONR7R8, SR7, SOR7, SO$_2$R7, SO$_2$NR7R8, NR7SO$_2$R7, $(C_1-C_6)$-alkylene-$(C_3-C_{10})$-cycloalkyl, $(C_1-C_6)$-alkylene-$(C_6-C_{10})$-aryl, $(C_1-C_6)$-alkylene-heterocycle, $(C_3-C_{10})$-cycloalkyl, $(C_6-C_{10})$-aryl and heterocycle with the further stipulation that not all the substituents R1, R2 and R3 may simultaneously be hydrogen or methyl,
R7 and R8 are independently selected from the group consisting of H, $(C_1-C_6)$-alkyl, $(C_3-C_{10})$-cycloalkyl, $(C_6-C_{10})$-aryl, heterocycle, $(C_1-C_6)$-alkylene-CONR9R10, $(C_1-C_6)$-alkylene-COOR9, $(C_1-C_6)$-alkylene-COR9, $(C_1-C_6)$-alkylene-OR9, $(C_1-C_6)$-alkylene-NR9R10, $(C_1-C_6)$-alkylene-SR9, $(C_1-C_6)$-alkylene-S(O)R9, $(C_{1-6})$-alkylene-S(O)$_2$R9, $(C_1-C_4)$-alkylene-$(C_6-C_{10})$-aryl and $(C_1-C_4)$-alkylene-heterocycle;
R9, R10 are independently selected from the group consisting of H, $(C_1-C_6)$-alkyl, $(C_1-C_6)$-alkylene-$(C_6-C_{10})$-aryl and $(C_1-C_6)$-alkylene-heterocycle;
R4 is selected from the group consisting of hydrogen, $(C_1-C_6)$-alkyl or $(C_3-C_8)$-cycloalkyl, where $(C_1-C_6)$-alkyl or $(C_3-C_8)$-cycloalkyl may be substituted by F, Cl, Br, I, CN, aryl, heterocycle, $NH_2$, NH$(C_1-C_6)$-alkyl, N$((C_1-C_6)$-alkyl)$_2$, OH, O$(C_1-C_6)$-alkyl, O-aryl, O-heteroaryl, S$(C_1-C_6)$-alkyl, S(O)$(C_1-C_6)$-alkyl, S(O)$_2(C_1-C_6)$-alkyl, where the alkyl groups may in each case be substituted by F, Cl, Br, I and where the aryl and heterocycle substituents may in each case be substituted one or more times by F, Cl, Br, I, CN, $NO_2$, $SF_5$, OH, $(C_1-C_6)$-alkyl, $-CF_3$, $-OCF_3$, $-SCF_3$, $(C_2-C_6)$-alkenyl, $(C_2-C_6)$-alkynyl, O$(C_1-C_4)$-alkyl, $NH_2$, NH$(C_1-C_4)$-alkyl, N$((C_1-C_4)$-alkyl)$_2$, NR7CONH$(C_1-C_4)$-alkyl, CO$(C_{1-4})$-alkyl, OCO$(C_1-C_4)$-alkyl, OCOO$(C_1-C_4)$-alkyl, COO$(C_1-C_4)$-alkyl, $CONH_2$, CONH$(C_1-C_4)$-alkyl, CON$((C_1-C_4)$-alkyl)$_2$, $(C_1-C_6)$-alkylene-O$(C_1-C_4)$-alkyl, $(C_1-C_6)$-alkylene-NH$(C_1-C_4)$-alkyl, $(C_1-C_6)$-alkylene-$NH_2$, $(C_1-C_6)$-alkylene-N$((C_1-C_4)$-alkyl)$_2$, $(C_{1-6})$-alkylene-NHSO$_2(C_1-C_4)$-alkyl, $(C_1-C_6)$-alkylene-S$(C_1-C_4)$-alkyl, alkylene-S(O)—(C1-C4)-alkyl, alkylene-$CONH_2$, alkylene-CONH$(C_1-C_4)$-alkyl, alkylene-CON$((C_1-C_4)$-alkyl)$_2$, S$(C_1-C_4)$-alkyl, SO$(C_1-C_4)$-alkyl, SO$_2(C_1-C_4)$-alkyl, $SO_2NH_2$, SO$_2$NH$(C_1-C_4)$-alkyl, SO$_2$N$((C_1-C_4)$-alkyl)$_2$, NR7SO$_2(C_1-C_4)$alkyl, $(C_1-C_6)$-alkylene-$(C_3-C_{10})$-cycloalkyl, $(C_3-C_{10})$-cycloalkyl;
R11, R12, R13, R14, R15 and R16 are independently selected from the group consisting of H, $(C_1-C_6)$-alkyl, aryl, heterocycle, $(C_3-C_8)$-cycloalkyl, $(C_1-C_4)$-alkylene-Oalkyl, $(C_1-C_4)$-alkylene-Salkyl, $(C_1-C_4)$-alkylene-NHalkyl, $(C_1-C_4)$-alkylene-N(alkyl)$_2$, $(C_1-C_4)$-alkylene-aryl, $(C_1-C_4)$-alkylene-heterocycle, F, Cl, Br, I, CN, COOH, COO$(C_1-C_6)$-alkyl, $CONH_2$, CONH$(C_1-C_6)$-alkyl, CON$((C_1-C_6)$-alkyl)$_2$, $CF_3$; where the aryl and heterocycle substituents may be substituted one or more times by F, Cl, Br, I, CN, $NO_2$, $SF_5$, OH, $(C_1-C_6)$-alkyl, $-CF_3$, $-OCF_3$, $-SCF_3$, $(C_2-C_6)$-alkenyl, $(C_2-C_6)$-alkynyl, O$(C_1-C_4)$-alkyl, $NH_2$, NH$(C_1-C_4)$-alkyl, N$((C_1-C_4)$-alkyl)$_2$, NR7CONH$(C_1-C_4)$-alkyl, CO$(C_1-C_4)$-alkyl, OCO$(C_1-C_4)$-alkyl, OCOO$(C_1-C_4)$-alkyl, COO$(C_1-C_4)$-alkyl, $CONH_2$, CONH$(C_1-C_4)$-alkyl, CON$((C_1-C_4)$-alkyl)$_2$, $(C_1-C_6)$-alkylene-O$(C_1-C_4)$-alkyl, $(C_1-C_6)$-alkylene-NH$(C_1-C_4)$-alkyl, $(C_1-C_6)$-alkylene-$NH_2$, $(C_1-C_6)$-alkylene-N$((C_1-C_4)$-alkyl)$_2$, $(C_1-C_6)$-alkylene-NHSO$_2(C_1-C_4)$-alkyl, $(C_1-C_6)$-alkylene-S$(C_1-C_4)$-alkyl, alkylene-S(O)—$(C_1-C_4)$-alkyl, alkylene-$CONH_2$, alkylene-CONH$(C_1-C_4)$-alkyl, alkylene-CON$((C_1-C_4)$-alkyl)$_2$, S$(C_1-C_4)$-alkyl, SO$(C_1-C_4)$-alkyl, SO$_2(C_1-C_4)$-alkyl, $SO_2NH_2$, SO$_2$NH$(C_1-C_4)$-alkyl, SO$_2$N$((C_1-C_4)$-alkyl)$_2$, NR7SO$_2(C_1-C_4)$-alkyl, $(C_1-C_6)$-alkylene-$(C_3-C_{10})$-cycloalkyl, $(C_3-C_{10})$-cycloalkyl; with the further stipulation that two of the substituents selected from the group comprising R4, R11, R12, R13, R14, R15 and R16 together form a $(C_2-C_6)$-alkylene substituent, to which a $(C_6-C_{10})$-aryl substituent or a $(C_6-C_{10})$-heterocycle substituent may be fused, wherein the $(C_2-C_6)$-alkylene substituent and the fused-on aryl substituents or heterocycle substituents may be substituted one or more times by F, Cl, Br, I, $OCF_3$, $CF_3$, CN, $(C_1-C_6)$-alkyl, aryl, heterocycle, $(C_3-C_8)$-cycloalkyl, $(C_1-C_4)$-alkylene-Oalkyl, $(C_1-C_4)$-alkylene-Salkyl, $(C_1-C_4)$-alkylene-NHalkyl, $(C_1-C_4)$-alkylene-N(alkyl)$_2$, $(C_1-C_4)$-alkylene-aryl, $(C_1-C_4)$-alkylene-heterocycle, COOH, COO$(C_1-C_6)$-alkyl, $CONH_2$, CONH$(C_1-C_6)$-alkyl, CON$((C_1-C_6)$-alkyl)$_2$, OH, O—$(C_1-C_6)$-alkyl, O—$(C_3-C_6)$-cycloalkyl, S—$(C_1-C_6)$-alkyl, S—$(C_3-C_6)$-cycloalkyl, SO—$(C_1-C_6)$-alkyl, SO—$(C_3-C_6)$-cycloalkyl, SO$_2$—$(C_1-C_6)$-alkyl, SO$_2$—$(C_3-C_6)$-cycloalkyl, SO$_2$—$NH_2$, SO$_2$—NH—$(C_1-C_6)$-alkyl, SO$_2$—NH—SO$_2$—$(C_3-C_6)$-cycloalkyl may be substituted; where the aryl and heterocycle substituents may be substituted one or more times by F, Cl, Br, I, CN, $NO_2$, $SF_5$, OH, $(C_1-C_6)$-alkyl, $-CF_3$, $-OCF_3$, $-SCF_3$, $(C_2-C_6)$-alkenyl, $(C_2-C_6)$-alkynyl, O$(C_1-C_4)$-alkyl, $NH_2$, NH$(C_1-C_4)$-alkyl, N$((C_1-C_4)$-alkyl)$_2$, NR7CONH$(C_1-C_4)$-alkyl, CO$(C_1-C_4)$-alkyl, OCO$(C_1-C_4)$-alkyl, OCOO$(C_1-C_4)$-alkyl, COO$(C_1-C_4)$-alkyl, $CONH_2$, CONH$(C_1-C_4)$-alkyl, CON$((C_1-C_4)$-alkyl)$_2$, $(C_{1-6})$-alkylene-O$(C_1-C_4)$-alkyl, $(C_{1-6})$-alkylene-NH$(C_{1-4})$-alkyl, $(C_1-C_6)$-alkylene-$NH_2$, $(C_1-C_6)$-alkylene-N$((C_1-C_4)$-alkyl)$_2$, $(C_1-C_6)$-alkylene-NHSO$_2(C_1-C_4)$-alkyl, $(C_1-C_6)$-alkylene-S$(C_1-C_4)$-alkyl, alkylene-S(O)—$(C_1-C_4)$-alkyl, alkylene-$CONH_2$, alkylene-CONH$(C_1-C_4)$-alkyl, alkylene-CON$((C_1-C_4)$-alkyl)$_2$, S$(C_1-C_4)$-alkyl, SO$(C_1-C_4)$-alkyl, SO$_2(C_1-C_4)$-alkyl, $SO_2NH_2$, SO$_2$NH$(C_1-C_4)$-alkyl, SO$_2$N$((C_1-C_4)$-alkyl)$_2$, NR7SO$_2(C_1-C_4)$-alkyl, $(C_1-C_6)$-alkylene-$(C_3-C_{10})$-cycloalkyl, $(C_3-C_{10})$-cycloalkyl;
n is 0 or 1; and with the further stipulation that the compound 1,3-di(cyclopropylmethyl)-7-(4-methoxybenzyl)-8-(4-piperidinyloxy)xanthine is excluded, and the pharmaceutically acceptable salts thereof.

Preferably, compounds of the present invention comprise those in which one or more of the substituents of formula I have the following meaning:
R1, R2 and R3 are independently selected from the group consisting of H, $(C_1-C_{10})$-alkyl, $(C_3-C_{10})$-cycloalkyl, $(C_2-C_{10})$-alkenyl, $(C_2-C_{10})$-alkynyl, $(C_6-C_{10})$-aryl, heterocycle, where the alkyl, cycloalkyl, alkenyl, alkynyl, aryl and heterocycle substituents may be substituted one or more times by F, Cl, Br, I, CN, $NO_2$, $SF_5$, OH, $(C_1-C_6)$-alkyl, $—CF_3$, $—OCF_3$, $—SCF_3$, $(C_2-C_6)$-alkenyl, $(C_2-C_6)$-alkynyl, OR7, $OP(O)(OR7)_2$, NR7R8, NR7CONR7R8, COR7, OCOR7, OCOOR7, COOR7, CONR7R8, OCONR7R8, $(C_1-C_6)$-alkylene-OR7, $(C_1-C_6)$-alkylene-NR7R8, $(C_1-C_6)$-alkylene-NR7SO2R7, $(C_1-C_6)$-alkylene-SR7, alkylene-S(O)R7, alkylene-CONR7R8, SR7, SOR7, $SO_2R7$, $SO_2NR7R8$, $NR7SO_2R7$, $(C_1-C_6)$-alkylene-$(C_3-C_{10})$-cycloalkyl, $(C_1-C_6)$-alkylene-$(C_6-C_{10})$-aryl, $(C_1-C_6)$-alkylene-heterocycle, $(C_3-C_{10})$-cycloalkyl, $(C_6-C_{10})$-aryl or heterocycle with the stipulation that not all the substituents R1, R2 and R3 may simultaneously be hydrogen or methyl;

R7 and R8 are independently selected from the group consisting of H, $(C_1-C_6)$-alkyl, $(C_3-C_{10})$-cycloalkyl, $(C_6-C_{10})$-aryl, heterocycle, $(C_1-C_6)$-alkylene-CONR9R10, $(C_1-C_6)$-alkylene-COOR9, $(C_1-C_6)$-alkylene-COR9, $(C_1-C_6)$-alkylene-OR9, $(C_1-C_6)$-alkylene-NR9R10, $(C_1-C_4)$-alkylene-$(C_6-C_{10})$-aryl and $(C_1-C_4)$-alkylene-heterocycle;

R9 and R10 are independently of one another selected from the group consisting of H, $(C_1-C_6)$-alkyl, $(C_1-C_6)$-alkylene-$(C_6-C_{10})$-aryl and, $(C_1-C_6)$-alkylene-heterocycle;

R4 hydrogen, $(C_1-C_6)$-alkyl or $(C_3-C_8)$-cycloalkyl, where $(C_1-C_6)$-alkyl or $(C_3-C_8)$-cycloalkyl may be substituted by F, Cl, Br, I, CN, aryl, heterocycle, $NH_2$, $NH(C_1-C_6)$-alkyl, $N((C_1-C_6)$-alkyl$)_2$, OH, $O(C_1-C_6)$-alkyl, O-aryl, O-heteroaryl, $S(C_1-C_6)$-alkyl, $S(O)(C_1-C_6)$-alkyl, $S(O)_2(C_1-C_6)$-alkyl; where the aryl and heterocycle groups may be substituted one or more times by F, Cl, Br, I, CN, $NO_2$, $SF_5$, OH, $(C_1-C_6)$-alkyl, $—CF_3$, $—OCF_3$, $—SCF_3$, $(C_2-C_6)$-alkenyl, $(C_2-C_6)$-alkynyl, $O(C_1-C_4)$-alkyl, $NH_2$, $NH(C_1-C_4)$-alkyl, $N((C_1-C_4)$-alkyl$)_2$, $NR7CONH(C_1-C_4)$-alkyl, $CO(C_1-C_4)$-alkyl, $OCO(C_1-C_4)$-alkyl, $OCOO(C_1-C_4)$-alkyl, $COO(C_1-C_4)$-alkyl, $CONH_2$, $CONH(C_1-C_4)$-alkyl, $CON((C_1-C_4)$-alkyl$)_2$, $(C_1-C_6)$-alkylene-$O(C_1-C_4)$-alkyl, $(C_1-C_6)$-alkylene-$NH(C_1-C_4)$-alkyl, $(C_1-C_6)$-alkylene-$NH_2$, $(C_{1-6})$-alkylene-$N((C_1-C_4)$-alkyl$)_2$, $(C_{1-6})$-alkylene-$NHSO_2(C_1-C_4)$-alkyl, $(C_1-C_6)$-alkylene-$S(C_1-C_4)$-alkyl, alkylene-S(O)—(C1-C4)-alkyl, alkylene-$CONH_2$, alkylene-$CONH(C_1-C_4)$-alkyl, alkylene-$CON((C_1-C_4)$-alkyl$)_2$, $S(C_1-C_4)$-alkyl, $SO(C_1-C_4)$-alkyl, $SO_2(C_1-C_4)$-alkyl, $SO_2NH_2$, $SO_2NH(C_1-C_4)$-alkyl, $SO_2N((C_1-C_4)$-alkyl$)_2$, $NR7SO_2(C_1-C_4)$-alkyl, $(C_1-C_6)$-alkylene-$(C_3-C_{10})$-cycloalkyl, and $(C_3-C_{10})$-cycloalkyl;

R11, R12, R13, R14, R15 and R16 are independently selected from the group consisting of H, $(C_1-C_6)$-alkyl, $(C_3-C_8)$-cycloalkyl, $(C_1-C_4)$-alkylene-O-alkyl, $(C_1-C_4)$-alkylene-S-alkyl, $(C_1-C_4)$-alkylene-NHalkyl, $(C_1-C_4)$-alkylene-N(alkyl)$_2$, $(C_1-C_4)$-alkylene-aryl, $(C_1-C_4)$-alkylene-heterocycle, F, Cl, Br, I, CN, COOH, $COO(C_1-C_6)$-alkyl, $CONH_2$, $CONH(C_1-C_6)$-alkyl, $CON((C_1-C_6)$-alkyl$)_2$, $CF_3$; with the stipulation that two of the substituents R4, R11, R12, R13, R14, R15 or R16 together form a $(C_2-C_6)$-alkylene wherein the $(C_2-C_6)$-alkylene may be substituted one or more times by F, Cl, Br, I, CN, $NO_2$, $SF_5$, OH, $(C_1-C_6)$-alkyl, $—CF_3$, $—OCF_3$, $—SCF_3$, $(C_2-C_6)$-alkenyl, $(C_2-C_6)$-alkynyl, $O(C_1-C_4)$-alkyl, $NH_2$, $NH(C_1-C_4)$-alkyl, $N((C_1-C_4)$-alkyl$)_2$, $NR7CONH(C_1-C_4)$-alkyl, $CO(C_1-C_4)$-alkyl, $OCO(C_1-C_4)$-alkyl, $OCOO(C_1-C_4)$-alkyl, $COO(C_1-C_4)$-alkyl, $CONH_2$, $CONH(C_1-C_4)$-alkyl, $CON((C_1-C_4)$-alkyl$)_2$, $(C_1-C_6)$-alkylene-$O(C_1-C_4)$-alkyl, $(C_1-C_6)$-alkylene-$NH(C_1-C_4)$-alkyl, $(C_1-C_6)$-alkylene-$NH_2$, $(C_1-C_6)$-alkylene-$N((C_1-C_4)$-alkyl$)_2$, $(C_{1-6})$-alkylene-$NHSO_2(C_1-C_4)$-alkyl, $(C_1-C_6)$-alkylene-$S(C_1-C_4)$-alkyl, alkylene-S(O)—(C1-C4)-alkyl, alkylene-$CONH_2$, alkylene-$CONH(C_1-C_4)$-alkyl, alkylene-$CON((C_1-C_4)$-alkyl$)_2$, $S(C_1-C_4)$-alkyl, $SO(C_1-C_4)$-alkyl, $SO_2(C_1-C_4)$-alkyl, $SO_2NH_2$, $SO_2NH(C_1-C_4)$-alkyl, $SO_2N((C_1-C_4)$-alkyl$)_2$, $NR7SO_2(C_1-C_4)$-alkyl, $(C_1-C_6)$-alkylene-$(C_3-C_{10})$-cycloalkyl, $(C_3-C_{10})$-cycloalkyl;

n is 0 or 1;

and, their pharmaceutically acceptable salts with the further stipulation that the compound 1,3-di(cyclopropylmethyl)-7-(4-methoxybenzyl)-8-(4-piperidinyloxy)xanthines is excluded therefrom Particularly preferred are those compounds of formula I in which one or more of the R-group substituents have the following meaning:

R1, R2 and R3 are independently selected from the group consisting of H, $(C_1-C_{10})$-alkyl, $(C_3-C_{10})$-cycloalkyl, $(C_2-C_{10})$-alkenyl, $(C_2-C_{10})$-alkynyl, $(C_6-C_{10})$-aryl, heterocycle, where the alkyl, cycloalkyl, alkenyl, alkynyl, aryl and heterocycle substituents may be substituted one or more times by F, Cl, Br, I, CN, $NO_2$, $SF_5$, OH, $(C_1-C_6)$-alkyl, $—CF_3$, $—OCF_3$, $—SCF_3$, $(C_2-C_6)$-alkenyl, $(C_2-C_6)$-alkynyl, OR7, $OP(O)(OR7)_2$, NR7R8, NR7CONR7R8, COR7, OCOR7, OCOOR7, COOR7, CONR7R8, OCONR7R8, $(C_1-C_6)$-alkylene-OR7, $(C_1-C_6)$-alkylene-NR7R8, $(C_1-C_6)$-alkylene-NR7SO2R7, $(C_1-C_6)$-alkylene-SR7, alkylene-S(O)R7, alkylene-CONR7R8, SR7, SOR7, $SO_2R7$, $SO_2NR7R8$, $NR7SO_2R7$, $(C_1-C_6)$-alkylene-$(C_3-C_{10})$-cycloalkyl, $(C_1-C_6)$-alkylene-$(C_6-C_{10})$-aryl, $(C_1-C_6)$-alkylene-heterocycle, $(C_3-C_{10})$-cycloalkyl, $(C_6-C_{10})$-aryl or heterocycle; with the stipulation that not all substituents R1, R2 and R3 may simultaneously be hydrogen or methyl;

R7, R8 are independently selected from the group consisting of H, $(C_1-C_6)$-alkyl, $(C_3-C_{10})$-cycloalkyl, aryl, heterocycle, $(C_1-C_4)$-alkylene-$(C_6-C_{10})$-aryl or $(C_1-C_4)$-alkylene-heterocycle;

R4 are independently selected from the group consisting of hydrogen, $(C_1-C_6)$-alkyl or $(C_3-C_8)$-cycloalkyl, where $(C_1-C_6)$-alkyl or $(C_3-C_8)$-cycloalkyl may be substituted by F, Cl, Br, I, CN, aryl, heterocycle, $NH_2$, $NH(C_1-C_6)$-alkyl, $N((C_1-C_6)$-alkyl$)_2$, OH, $O(C_1-C_6)$-alkyl, O-aryl, O-heteroaryl, $S(C_1-C_6)$-alkyl, $S(O)(C_1-C_6)$-alkyl, $S(O)_2(C_1-C_6)$-alkyl;

R11, R12, R13, R14, R15, R16 are independently selected from the group consisting of H, $(C_1-C_6)$-alkyl, $(C_3-C_8)$-cycloalkyl, $(C_1-C_4)$-alkylene-aryl or $(C_1-C_4)$-alkylene-heterocycle with the additional stipulation that two of the substituents R4, R11, R12, R13, R14, R15, R16 together form a $(C_2-C_6)$-alkylene substituent;

n is 0;

with the further stipulation that the compound 1,3-di(cyclopropylmethyl)-7-(4-methoxybenzyl)-8-(4-piperidinyloxy)xanthines is excluded, and the pharmaceutically acceptable salts thereof.

More preferably, compounds of the present invention comprise compounds of formula I in which one or more of the R-group substituents have the following meaning:

R1, R2 and, R3 are independently selected from the group consisting of $(C_1-C_6)$-alkyl, $(C_3-C_{10})$-cycloalkyl, $(C_2-C_{10})$-alkenyl, $(C_2-C_{10})$-alkynyl, $(C_6-C_{10})$-aryl, heterocycle, where the alkyl, cycloalkyl, alkenyl, alkynyl, aryl and heterocycle groups may be substituted one or more times by F, Cl, Br, CN, $NO_2$, $SF_5$, OH, $(C_1-C_6)$-alkyl, $—CF_3$, $—OCF_3$, $—SCF_3$, $(C_2-C_6)$-alkenyl, $(C_2-C_6)$-alkynyl, OR7, NR7R8, NR7CONR7R8, COR7, COOR7, CONR7R8, $(C_1-C_6)$-alkylene-OR7, $(C_1-C_6)$-alkylene-NR7R8, $(C_1-C_6)$-alkylene-NR7SO$_2$R7, $(C_1-C_6)$-alkylene-SR7, alkylene-S(O)R7, alkylene-CONR7R8, SR7, SOR7, SO$_2$R7, SO$_2$NR7R8, NR7SO$_2$R7, $(C_1-C_6)$-alkylene-$(C_3-C_{10})$-cycloalkyl, $(C_1-C_6)$-alkylene-$(C_6-C_{10})$-aryl, $(C_1-C_6)$-alkylene-heterocycle, $(C_3-C_{10})$-cycloalkyl, $(C_6-C_{10})$-aryl and $(C_6-C_{10})$-heterocycle with the further stipulation that not all the R1, R2 and R3 substituents may simultaneously be methyl;

R7 and R8 are independently selected from the group consisting of H, $(C_1-C_6)$-alkyl, $(C_3-C_{10})$-cycloalkyl, aryl, heterocycle $(C_1-C_4)$-alkylene-$(C_6-C_{10})$-aryl or $(C_1-C_4)$-alkylene-heterocycle;

R4 is hydrogen;

R11, R12, R13 and, R14 are independently selected from the group consisting of H, $(C_1-C_6)$-alkyl or $C_3-C_7$-cycloalkyl, $(C_1-C_4)$-alkylene-aryl and $(C_1-C_4)$-alkylene-heterocycle; and, n is 0;

and a pharmaceutically acceptable salt thereof.

Most preferably compounds of the present invention comprise those compounds of formula I in which one or more of the R-group substituents have the following meaning:

R1, R2 and R3 are independently selected from the group consisting of $(C_1-C_6)$-alkyl, $(C_3-C_{10})$-cycloalkyl, $(C_2-C_{10})$-alkenyl, $(C_2-C_{10})$-alkynyl, $(C_6-C_{10})$-aryl, heterocycle, where the alkyl, cycloalkyl, alkenyl, alkynyl, aryl and heterocycle substituents may be substituted one or more times by F, Cl, CN, SF$_5$, $(C_1-C_6)$-alkyl, —CF$_3$, —OCF$_3$, —SCF$_3$, $(C_2-C4)$-alkenyl, $(C_2-C4)$-alkynyl, OR7, NR7R8, NR7CONR7R8, COR7, COOR7, CONR7R8, $(C_1-C4)$-alkylene-OR7, $(C_1-C4)$-alkylene-NR7R8, $(C_1-C4)$-alkylene-NR7SO$_2$R7, $(C_1-C4)$-alkylene-SR7, alkylene-S(O)R7, alkylene-CONR7R8, SR7, SOR7, SO$_2$R7, SO$_2$NR7R8, NR7SO$_2$R7, $(C_1-C_6)$-alkylene-$(C_3-C_{10})$-cycloalkyl, $(C_1-C_6)$-alkylene-$(C_6-C_{10})$-aryl, $(C_1-C_6)$-alkylene-heterocycle, $(C_3-C_{10})$-cycloalkyl, $(C_6-C_{10})$-aryl or heterocycle; with the further stipulation that not all the R1, R2 and R3 substituents may simultaneously be methyl;

R7 and, R8 are independently selected from the group consisting of H, $(C_1-C_6)$-alkyl, $(C_3-C_{10})$-cycloalkyl, aryl, heterocycle, $(C_1-C_4)$-alkylene-$(C_6-C_{10})$-aryl or $(C_1-C_4)$-alkylene-heterocycle;

R4 is hydrogen;

R11, R12, R13 and R14 are independently of one another H or $(C_1-C_4)$-alkyl;

n is 0;

and a pharmaceutically acceptable salt thereof.

The invention relates to compounds of the formula I in the form of their racemates, racemic mixtures and pure enantiomers and to their diastereomers and mixtures thereof.

If the R-group substituents may occur more than once in the compounds of the formula I, they may all, independently of one another, have the stated meanings and be identical or different.

The alkyl, alkenyl, alkynyl groups comprising the substituents R1, R2, R3, R4, R5, R6, R7, R8, R9, R10, R11 and R12 may be either straight-chain or branched.

For the purpose of this application, the following definitions apply as are known in the chemical arts. Aryl means an aromatic carbocyclic mono- or bicyclic ring system which comprises 6 to 10 atoms in the ring or rings.

Heteroaryl means a mono- or bicyclic aromatic ring system having 4 to 11 ring members, in which at least one atom in the ring system is a heteroatom from the series N, O and S.

An alkyl substituent means a straight-chain or branched hydrocarbon chain having one or more carbons, such as, for example, methyl, ethyl, isopropyl, tert-butyl, hexyl. The alkyl substituents may be substituted one or more times by suitable groups such as, for example, F, Cl, Br, I, CF$_3$, NO$_2$, N$_3$, CN, COOH, COO$(C_1-C_6)$alkyl, CONH$_2$, CONH$(C_1-C_6)$alkyl, CON[$(C_1-C_6)$alkyl]$_2$, cycloalkyl, $(C_2-C_6)$-alkenyl, $(C_2-C_6)$-alkynyl, O—$(C_1-C_6)$-alkyl O—CO—$(C_1-C_6)$-alkyl, O—CO—$(C_1-C_6)$-aryl, O—CO—$(C_1-C_6)$-heterocycle; PO$_3$H$_2$, SO$_3$H, SO$_2$—NH$_2$, SO$_2$NH$(C_1-C_6)$-alkyl, SO$_2$N[$(C_1-C_6)$-alkyl]$_2$, S—$(C_1-C_6)$-alkyl, S—$(CH_2)_n$-aryl, S—$(CH_2)_n$-heterocycle, SO—$(C_1-C_6)$-alkyl, SO—$(CH_2)_n$-aryl, SO—$(CH_2)_n$-heterocycle, SO$_2$—$(C_1-C_6)$-alkyl, SO$_2$—$(CH_2)_n$-aryl, SO$_2$—$(CH_2)_n$-heterocycle, SO$_2$—NH$(CH_2)_n$-aryl, SO$_2$—NH$(CH_2)_n$-heterocycle, SO$_2$—N$(C_1-C_6)$-alkyl)$(CH_2)_n$-aryl, SO$_2$—N$(C_1-C_6)$-alkyl)$(CH_2)_n$-heterocycle, SO$_2$—N$((CH_2)_n$-aryl)$_2$, SO$_2$—N$((CH_2)_n$-(heterocycle)$_2$ where n may be 0-6, and the aryl substituent or heterocyclic substituent may be substituted up to twice by F, Cl, Br, OH, CF$_3$, NO$_2$, CN, OCF$_3$, O—$(C_1-C_6)$-alkyl, $(C_1-C_6)$-alkyl, NH$_2$; C(NH)(NH$_2$), NH$_2$, NH—$(C_1-C_6)$-alkyl, N($(C_1-C_6)$-alkyl)$_2$, NH$(C_1-C_7)$-acyl, NH—CO—$(C_1-C_6)$-alkyl, NH—COO—$(C_1-C_6)$-alkyl, NH—CO-aryl, NH—CO-heterocycle, NH—COO-aryl, NH—COO-heterocycle, NH—CO—NH—$(C_1-C_6)$-alkyl, NH—CO—NH-aryl, NH—CO—NH-heterocycle, N$(C_1-C_6)$-alkyl —CO—$(C_1-C_6)$-alkyl, N$(C_1-C_6)$-alkyl —COO—$(C_1-C_6)$-alkyl, N$(C_1-C_6)$-alkyl —CO-aryl, N$(C_1-C_6)$-alkyl —CO-heterocycle, N$(C_1-C_6)$-alkyl —COO-aryl, N$(C_1-C_6)$-alkyl —COO-heterocycle, N$(C_1-C_6)$-alkyl —CO—NH—$(C_1-C_6)$-alkyl, N$(C_1-C_6)$-alkyl —CO—NH-aryl, N$(C_1-C_6)$-alkyl —CO—NH-heterocycle, N$((C_1-C_6)$-alkyl)-CO—N—$(C_1-C_6)$-alkyl)$_2$, N$((C_1-C_6)$-alkyl)-CO—N$((C_1-C_6)$-alkyl)-aryl, N$((C_1-C_6)$-alkyl)-CO—N$((C_1-C_6)$-alkyl)-heterocycle, N$((C_1-C_6)$-alkyl)-CO—N-(aryl)$_2$, N$((C_1-C_6)$-alkyl)-CO—N-(heterocycle)$_2$, N(aryl)-CO—$(C_1-C_6)$-alkyl, N(heterocycle)-CO—$(C_1-C_6)$-alkyl, N(aryl)-COO—$(C_1-C_6)$-alkyl, N(heterocycle)-COO—$(C_1-C_6)$-alkyl, N(aryl)-CO-aryl, N(heterocycle)-CO-aryl, N(aryl)-COO-aryl, N(heterocycle)-COO-aryl, N(aryl)-CO—NH—$(C_1-C_6)$-alkyl), N(heterocycle)-CO—NH—$(C_1-C_6)$-alkyl), N(aryl)-CO—NH-aryl, N(heterocycle)-CO—NH-aryl, N(aryl)-CO—N—$(C_1-C_6)$-alkyl)$_2$, N(heterocycle)-CO—N—$(C_1-C_6)$-alkyl)$_2$, N(aryl)-CO—N$((C_1-C_6)$-alkyl)-aryl, N(heterocycle)-CO—N$((C_1-C_6)$-alkyl)-aryl, N(aryl)-CO—N-(aryl)$_2$, N(heterocycle)-CO—N-(aryl)$_2$, aryl, O—$(CH_2)_n$-aryl, O—$(CH_2)_n$-heterocycle, where n may be 0-6, where the aryl substituent or heterocyclic substituent may be substituted one to 3 times by F, Cl, Br, I, OH, CF$_3$, NO$_2$, CN, OCF$_3$, O—$(C_1-C_6)$-alkyl, $(C_1-C_6)$-alkyl, NH$_2$, NH$(C_1-C_6)$-alkyl, N$((C_1-C_6)$-alkyl)$_2$, SO$_2$—CH$_3$, COOH, COO—$(C_1-C_6)$-alkyl, and CONH$_2$.

An alkenyl substituent means a straight-chain or branched hydrocarbon chain having two or more carbons and one or more double bonds, such as, for example, vinyl, allyl, and pentenyl. The alkenyl substituents may be substituted one or more times by suitable groups such as, for example: F, Cl, Br, I, CF$_3$, NO$_2$, N$_3$, CN, COOH, COO$(C_1-C_6)$alkyl, CONH$_2$, CONH$(C_1-C_6)$alkyl, CON[$(C_1-C_6)$alkyl]$_2$, cycloalkyl, $(C_1-C_{10})$-alkyl, $(C_2-C_6)$-alkynyl, O—$(C_1-C_6)$-alkyl O—CO—$(C_1-C_6)$-alkyl, O—CO—$(C_1-C_6)$-aryl, O—CO—$(C_1-C_6)$-heterocycle; PO$_3$H$_2$, SO$_3$H, SO$_2$—NH$_2$, SO$_2$NH$(C_1-C_6)$-alkyl, SO$_2$N[$(C_1-C_6)$-alkyl]$_2$, S—$(C_1-C_6)$-alkyl, S—$(CH_2)_n$-aryl, S—$(CH_2)_n$-heterocycle, SO—$(C_1-C_6)$-alkyl, SO—$(CH_2)_n$-aryl, SO—$(CH_2)_n$-heterocycle, SO$_2$—$(C_1-C_6)$-alkyl, SO$_2$—$(CH_2)_n$-aryl, SO$_2$—$(CH_2)_n$-heterocycle, SO$_2$NH$(CH_2)_n$-aryl, SO$_2$—NH$(CH_2)_n$-heterocycle, SO$_2$—N$(C_1-C_6)$-alkyl)$(CH_2)_n$-aryl, SO$_2$—N$(C_1-C_6)$-alkyl)$(CH_2)_n$-heterocycle, $SO_2$—$N((CH_2)_n$-aryl$)_2$, $SO_2$—$N((CH_2)_n$-(heterocycle)$_2$ where n may be 0-6, and the aryl substituent or heterocyclic substituent may be substituted up to twice by F, Cl, Br, OH, $CF_3$, $NO_2$, CN, $OCF_3$, O—($C_1$-$C_6$)-alkyl, ($C_1$-$C_6$)-alkyl, $NH_2$; C(NH)($NH_2$), $NH_2$, NH—($C_1$-$C_6$)-alkyl, N(($C_1$-$C_6$)-alkyl)$_2$, NH($C_1$-$C_7$)-acyl, NH—CO—($C_1$-$C_6$)-alkyl, NH—COO—($C_1$-$C_6$)-alkyl, NH—CO-aryl, NH—CO-heterocycle, NH—COO-aryl, NH—COO-heterocycle, NH—CO—NH—($C_1$-$C_6$)-alkyl, NH—CO—NH-aryl, NH—CO—NH-heterocycle, N($C_1$-$C_6$)-alkyl —CO—($C_1$-$_6$)-alkyl, N($C_1$-$C_6$)-alkyl —COO—($C_1$-$_6$)-alkyl, N($C_1$-$C_6$)-alkyl —CO-aryl, N($C_1$-$C_6$)-alkyl —CO-heterocycle, N($C_1$-$C_6$)-alkyl —COO-aryl, N($C_1$-$C_6$)-alkyl —COO-heterocycle, N($C_1$-$C_6$)-alkyl —CO—NH—($C_1$-$C_6$)-alkyl), N($C_1$-$C_6$)-alkyl —CO—NH-aryl, N($C_1$-$C_6$)-alkyl —CO—NH-heterocycle, N(($C_1$-$C_6$)-alkyl)-CO—N—($C_1$-$C_6$)-alkyl)$_2$, N(($C_1$-$C_6$)-alkyl)-CO—N(($C_1$-$C_6$)-alkyl)-aryl, N(($C_1$-$C_6$)-alkyl)-CO—N(($C_1$-$C_6$)-alkyl)-heterocycle, N(($C_1$-$C_6$)-alkyl)-CO—N-(aryl)$_2$, N(($C_1$-$C_6$)-alkyl)-CO—N-(heterocycle)$_2$, N(aryl)-CO—($C_1$-$C_6$)-alkyl, N(heterocycle)-CO—($C_1$-$C_6$)-alkyl, N(aryl)-COO—($C_1$-$C_6$)-alkyl, N(heterocycle)-COO—($C_1$-$C_6$)-alkyl, N(aryl)-CO-aryl, N(heterocycle)-CO-aryl, N(aryl)-COO-aryl, N(heterocycle)-COO-aryl, N(aryl)-CO—NH—($C_1$-$C_6$)-alkyl), N(heterocycle)-CO—NH—($C_1$-$C_6$)-alkyl), N(aryl)-CO—NH-aryl, N(heterocycle)-CO—NH-aryl, N(aryl)-CO—N—($C_1$-$C_6$)-alkyl)$_2$, N(heterocycle)-CO—N—($C_1$-$C_6$)-alkyl)$_2$, N(aryl)-CO—N(($C_1$-$C_6$)-alkyl)-aryl, N(heterocycle)-CO—N(($C_1$-$C_6$)-alkyl)-aryl, N(aryl)-CO—N-(aryl)$_2$, N(heterocycle)-CO—N-(aryl)$_2$, aryl, O—($CH_2$)$_n$-aryl, O—($CH_2$)$_n$-heterocycle, where n may be 0-6, where the aryl substituent or heterocyclic substituent may be substituted one to 3 times by F, Cl, Br, I, OH, $CF_3$, $NO_2$, CN, $OCF_3$, O—($C_1$-$C_6$)-alkyl, ($C_1$-$C_6$)-alkyl, $NH_2$, NH($C_1$-$C_6$)-alkyl, N(($C_1$-$C_6$)-alkyl)$_2$, $SO_2$—$CH_3$, COOH, COO—($C_1$-$C_6$)-alkyl, $CONH_2$.

An alkynyl substituent means a straight-chain or branched hydrocarbon chain having two or more carbons and one or more triple bonds, such as, for example, ethynyl, propynyl, hexynyl. The alkynyl substituents may be substituted one or more times by suitable groups such as, for example: F, Cl, Br, I, $CF_3$, $NO_2$, $N_3$, CN, COOH, COO($C_1$-$C_6$)alkyl, $CONH_2$, CONH($C_1$-$C_6$)alkyl, CON[($C_1$-$C_6$)alkyl]$_2$, cycloalkyl, ($C_2$-$C_6$)-alkenyl, ($C_1$-$C_{10}$)-alkyl, O—($C_1$-$C_6$)-alkyl O—CO—($C_1$-$C_6$)-alkyl, O—CO—($C_1$-$C_6$)-aryl, O—CO—($C_1$-$C_6$)-heterocycle; $PO_3H_2$, $SO_3H$, $SO_2$—$NH_2$, $SO_2NH$($C_1$-$C_6$)-alkyl, $SO_2N$[($C_1$-$C_6$)-alkyl]$_2$, S—($C_1$-$C_6$)-alkyl, S—($CH_2$)$_n$-aryl, S—($CH_2$)$_n$-heterocycle, SO—($C_1$-$C_6$)-alkyl, SO—($CH_2$)$_n$-aryl, SO—($CH_2$)$_n$-heterocycle, $SO_2$—($C_1$-$C_6$)-alkyl, $SO_2$—($CH_2$)$_n$-aryl, $SO_2$—($CH_2$)$_n$-heterocycle, $SO_2$—NH($CH_2$)$_n$-aryl, $SO_2$—NH($CH_2$)$_n$-heterocycle, $SO_2$—N($C_1$-$C_6$)-alkyl)($CH_2$)$_n$-aryl, $SO_2$—N($C_1$-$C_6$)-alkyl)($CH_2$)$_n$-heterocycle, $SO_2$—N(($CH_2$)$_n$-aryl)$_2$, $SO_2$—N(($CH_2$)$_n$-(heterocycle)$_2$ where n may be 0-6, and the aryl substituent or heterocyclic substituent may be substituted up to twice by F, Cl, Br, OH, $CF_3$, $NO_2$, CN, $OCF_3$, O—($C_1$-$C_6$)-alkyl, ($C_1$-$C_6$)-alkyl, $NH_2$;

C(NH)($NH_2$), $NH_2$, NH—($C_1$-$C_6$)-alkyl, N(($C_1$-$C_6$)-alkyl)$_2$, NH($C_1$-$C_7$)-acyl, NH—CO—($C_1$-$C_6$)-alkyl, NH—COO—($C_1$-$C_6$)-alkyl, NH—CO-aryl, NH—CO-heterocycle, NH—COO-aryl, NH—COO-heterocycle, NH—CO—NH—($C_1$-$C_6$)-alkyl, NH—CO—NH-aryl, NH—CO—NH-heterocycle, N($C_1$-$C_6$)-alkyl —CO—($C_1$-$C_6$)-alkyl, N($C_1$-$C_6$)-alkyl —COO—($C_1$-$C_6$)-alkyl, N($C_1$-$C_6$)-alkyl —CO-aryl, N($C_1$-$C_6$)-alkyl —CO-heterocycle, N($C_1$-$C_6$)-alkyl —COO-aryl, N($C_1$-$C_6$)-alkyl —COO-heterocycle, N($C_1$-$C_6$)-alkyl —CO—NH—($C_1$-$C_6$)-alkyl), N($C_1$-$C_6$)-alkyl —CO—NH-aryl, N($C_1$-$C_6$)-alkyl —CO—NH-heterocycle, N(($C_1$-$C_6$)-alkyl)-CO—N—($C_1$-$C_6$)-alkyl)$_2$, N(($C_1$-$C_6$)-alkyl)-CO—N(($C_1$-$C_6$)-alkyl)-aryl, N(($C_1$-$C_6$)-alkyl)-CO—N(($C_1$-$C_6$)-alkyl)-heterocycle, N(($C_1$-$C_6$)-alkyl)-CO—N-(aryl)$_2$, N(($C_1$-$C_6$)-alkyl)-CO—N-(heterocycle)$_2$, N(aryl)-CO—($C_1$-$C_6$)-alkyl, N(heterocycle)-CO—($C_1$-$C_6$)-alkyl, N(aryl)-COO—($C_1$-$C_6$)-alkyl, N(heterocycle)-COO—($C_1$-$C_6$)-alkyl, N(aryl)-CO-aryl, N(heterocycle)-CO-aryl, N(aryl)-COO-aryl, N(heterocycle)-COO-aryl, N(aryl)-CO—NH—($C_1$-$C_6$)-alkyl), N(heterocycle)-CO—NH—($C_1$-$C_6$)-alkyl), N(aryl)-CO—NH-aryl, N(heterocycle)-CO—NH-aryl, N(aryl)-CO—N—($C_1$-$C_6$)-alkyl)$_2$, N(heterocycle)-CO—N—($C_1$-$C_6$)-alkyl)$_2$, N(aryl)-CO—N(($C_1$-$C_6$)-alkyl)-aryl, N(heterocycle)-CO—N(($C_1$-$C_6$)-alkyl)-aryl, N(aryl)-CO—N-(aryl)$_2$, N(heterocycle)-CO—N-(aryl)$_2$, aryl, O—($CH_2$)$_n$-aryl, O—($CH_2$)$_n$-heterocycle, where n may be 0-6, where the aryl substituent or heterocyclic substituent may be substituted one to 3 times by F, Cl, Br, I, OH, $CF_3$, $NO_2$, CN, $OCF_3$, O—($C_1$-$C_6$)-alkyl, ($C_1$-$C_6$)-alkyl, $NH_2$, NH($C_1$-$C_6$)-alkyl, N(($C_1$-$C_6$)-alkyl)$_2$, $SO_2$—$CH_3$, COOH, COO—($C_1$-$C_6$)-alkyl, $CONH_2$.

An aryl substituent means a phenyl, naphthyl-, biphenyl-, tetrahydronaphthyl-, alpha- or beta-tetralon-, indanyl- or indan-1-on-yl substituent. The aryl substituents may be substituted one or more times by suitable groups such as, for example: F, Cl, Br, I, $CF_3$, $NO_2$, $N_3$, CN, COOH, COO($C_1$-$C_6$)alkyl, $CONH_2$, CONH($C_1$-$C_6$)alkyl, CON[($C_1$-$C_6$)alkyl]$_2$, cycloalkyl, ($C_1$-$C_{10}$)-alkyl, ($C_2$-$C_6$)-alkenyl, ($C_2$-$C_6$)-alkynyl, O—($C_1$-$C_6$)-alkyl O—CO—($C_1$-$C_6$)-alkyl, O—CO—($C_1$-$C_6$)-aryl, O—CO—($C_1$-$C_6$)-heterocycle;

$PO_3H_2$, $SO_3H$, $SO_2$—$NH_2$, $SO_2NH$($C_1$-$C_6$)-alkyl, $SO_2N$[($C_1$-$C_6$)-alkyl]$_2$, S—($C_1$-$C_6$)-alkyl, S—($CH_2$)$_n$-aryl, S—($CH_2$)$_n$-heterocycle, SO—($C_1$-$C_6$)-alkyl, SO—($CH_2$)$_n$-aryl, SO—($CH_2$)$_n$-heterocycle, $SO_2$—($C_1$-$C_6$)-alkyl, $SO_2$—($CH_2$)$_n$-aryl, $SO_2$—($CH_2$)$_n$-heterocycle, $SO_2$—NH($CH_2$)$_n$-aryl, $SO_2$—NH($CH_2$)$_n$-heterocycle, $SO_2$—N($C_1$-$C_6$)-alkyl)($CH_2$)$_n$-aryl, $SO_2$—N($C_1$-$C_6$)-alkyl)($CH_2$)$_n$-heterocycle, $SO_2$—N(($CH_2$)$_n$-aryl)$_2$, $SO_2$—N(($CH_2$)$_n$-(heterocycN($C_1$-$C_6$)-alkyl)($CH_2$)$_n$-heterocycle, $SO_2$—N(($CH_2$)$_n$-aryl)$_2$, $SO_2$—N(($CH_2$)$_n$-(heterocycle)$_2$ where n may be 0-6, and the aryl substituent or heterocyclic substituent may be substituted up to twice by F, Cl, Br, OH, $CF_3$, $NO_2$, CN, $OCF_3$, O—($C_1$-$C_6$)-alkyl, ($C_1$-$C_6$)-alkyl, $NH_2$; C(NH)($NH_2$), $NH_2$, NH—($C_1$-$C_6$)-alkyl, N(($C_1$-$C_6$)-alkyl)$_2$, NH($C_1$-$C_7$)-acyl, NH—CO—($C_1$-$C_6$)-alkyl, NH—COO—($C_1$-$C_6$)-alkyl, NH—CO-aryl, NH—CO-heterocycle, NH—COO-aryl, NH—COO-heterocycle, NH—CO—NH—($C_1$-$C_6$)-alkyl, NH—CO—NH-aryl, NH—CO—NH-heterocycle, N($C_1$-$C_6$)-alkyl —CO—($C_1$-$C_6$)-alkyl, N($C_1$-$C_6$)-alkyl —COO—($C_1$-$C_6$)-alkyl, N($C_1$-$C_6$)-alkyl —CO-aryl, N($C_1$-$C_6$)-alkyl —CO-heterocycle, N($C_1$-$C_6$)-alkyl —COO-aryl, N($C_1$-$C_6$)-alkyl —COO-heterocycle, N($C_1$-$C_6$)-alkyl —CO—NH—($C_1$-$C_6$)-alkyl), N($C_1$-$C_6$)-alkyl —CO—NH-aryl, N($C_1$-$C_6$)-alkyl —CO—NH-heterocycle, N(($C_1$-$C_6$)-alkyl)-CO—N—($C_1$-$C_6$)-alkyl)$_2$, N(($C_1$-$C_6$)-alkyl)-CO—N(($C_1$-$C_6$)-alkyl)-aryl, N(($C_1$-$C_6$)-alkyl)-CO—N(($C_1$-$C_6$)-alkyl)-heterocycle, N(($C_1$-$C_6$)-alkyl)-CO—N-(aryl)$_2$, N(($C_1$-$C_6$)-alkyl)-CO—N-(heterocycle)$_2$, N(aryl)-CO—($C_1$-$C_6$)-alkyl, N(heterocycle)-CO—($C_1$-$C_6$)-alkyl, N(aryl)-COO—($C_1$-$C_6$)-alkyl, N(heterocycle)-COO—($C_1$-$C_6$)-alkyl, N(aryl)-CO-aryl, N(heterocycle)-CO-aryl, N(aryl)-COO-aryl, N(heterocycle)-COO-aryl, N(aryl)-CO—NH—($C_1$-$C_6$)-alkyl), N(heterocycle)-CO—NH—($C_1$-$C_6$)-alkyl), N(aryl)-CO—NH-aryl, N(heterocycle)-CO—NH-aryl, N(aryl)-CO—N—($C_1$-$C_6$)-alkyl)$_2$, N(heterocycle)-CO—N—($C_1$-$C_6$)-alkyl)$_2$, N(aryl)-CO—N(($C_1$-$C_6$)-alkyl)-aryl, N(heterocycle)-CO—N(($C_1$-$C_6$)-alkyl)-aryl, N(aryl)-CO—N-(aryl)$_2$, N(heterocycle)-CO—N-(aryl)$_2$, aryl, O—($CH_2$)$_n$-aryl, O—($CH_2$)$_n$- heterocycle, where n may be 0-6, where the aryl substituent or heterocyclic substituent may be substituted one to 3 times by F, Cl, Br, I, OH, $CF_3$, $NO_2$, CN, $OCF_3$, O—$(C_1-C_6)$-alkyl, $(C_1-C_6)$-alkyl, $NH_2$, $NH(C_1-C_6)$-alkyl, $N((C_1-C_6)$-alkyl$)_2$, $SO_2$—$CH_3$, COOH, COO—$(C_1-C_6)$-alkyl, $CONH_2$.

where n may be 0-6, and the aryl substituent or heterocyclic substituent may be substituted up to twice by F, Cl, Br, OH, $CF_3$, $NO_2$, CN, $OCF_3$, O—$(C_1-C_6)$-alkyl, $(C_1-C_6)$-alkyl, $NH_2$; C(NH)($NH_2$), $NH_2$, NH—$(C_1-C_6)$-alkyl, $N((C_1-C_6)$-alkyl$)_2$, $NH(C_1-C_7)$-acyl, NH—CO—$(C_1-C_6)$-alkyl, NH—COO—$(C_1-C_6)$-alkyl, NH—CO-aryl, NH—CO-heterocycle, NH—COO-aryl, NH—COO-heterocycle, NH—CO—NH—$(C_1-C_6)$-alkyl, NH—CO—NH-aryl, NH—CO—NH-heterocycle, $N(C_1-C_6)$-alkyl —CO—$(C_1-C_6)$-alkyl, $N(C_1-C_6)$-alkyl —COO—$(C_1-C_6)$-alkyl, $N(C_1-C_6)$-alkyl —CO-aryl, $N(C_1-C_6)$-alkyl —CO-heterocycle, $N(C_1-C_6)$-alkyl —COO-aryl, $N(C_1-C_6)$-alkyl —COO-heterocycle, $N(C_1-C_6)$-alkyl -CO—NH—$(C_1-C_6)$-alkyl), $N(C_1-C_6)$-alkyl —CO—NH-aryl, $N(C_1-C_6)$-alkyl —CO—NH-heterocycle, $N((C_1-C_6)$-alkyl)-CO—N—$(C_1-C_6)$-alkyl$)_2$, $N((C_1-C_6)$-alkyl)-CO—N($(C_1-C_6)$-alkyl)-aryl, $N((C_1-C_6)$-alkyl)-CO—N($(C_1-C_6)$-alkyl)-heterocycle, $N((C_1-C_6)$-alkyl)-CO—N-(aryl)$_2$, $N((C_1-C_6)$-alkyl)-CO—N-(heterocycle)$_2$, N(aryl)-CO—$(C_1-C_6)$-alkyl, N(heterocycle)-CO—$(C_1-C_6)$-alkyl, N(aryl)-COO—$(C_1-C_6)$-alkyl, N(heterocycle)-COO—$(C_1-C_6)$-alkyl, N(aryl)-CO-aryl, N(heterocycle)-CO-aryl, N(aryl)-COO-aryl, N(heterocycle)-COO-aryl, N(aryl)-CO—NH—$(C_1-C_6)$-alkyl), N(heterocycle)-CO—NH—$(C_1-C_6)$-alkyl), N(aryl)-CO—NH-aryl, N(heterocycle)-CO—NH-aryl, N(aryl)-CO—N$(C_1-C_6)$-alkyl$)_2$, N(heterocycle)-CO—N—$(C_1-C_6)$-alkyl$)_2$, N(aryl)-CO—N($(C_1-C_6)$-alkyl)-aryl, N(heterocycle)-CO—N($(C_1-C_6)$-alkyl)-aryl, N(aryl)-CO—N-(aryl)$_2$, N(heterocycle)-CO—N-(aryl)$_2$, aryl, O—$(CH_2)_2$-aryl, O—$(CH_2)_n$-heterocycle, where n may be 0-6, where the aryl substituent or heterocyclic substituent may be substituted one to 3 times by F, Cl, Br, I, OH, $CF_3$, $NO_2$, CN, $OCF_3$, O—$(C_1-C_6)$-alkyl, $(C_1-C_6)$-alkyl, $NH_2$, $NH(C_1-C_6)$-alkyl, $N((C_1-C_6)$-alkyl$)_2$, $SO_2$—$CH_3$, COOH, COO—$(C_1-C_6)$-alkyl, $CONH_2$.

A cycloalkyl substituent means a ring system which comprises one or more rings, which is in saturated or partially unsaturated (with one or two double bonds) form and which is composed exclusively of carbon atoms, such as, for example, cyclopropyl, cyclopentyl, cyclopentenyl, cyclohexyl or adamantyl.

The cycloalkyl substituents substituents may be substituted one or more times by suitable groups such as, for example: F, Cl, Br, I, $CF_3$, $NO_2$, $N_3$, CN, COOH, COO($C_1$-$C_6$)alkyl, $CONH_2$, $CONH(C_1-C_6)$alkyl, CON[$(C_1-C_6)$alkyl]$_2$, cycloalkyl, $(C_1-C_{10})$-alkyl, $(C_2-C_6)$-alkenyl, $(C_2-C_6)$-alkynyl, O—$(C_1-C_6)$-alkyl O—CO—$(C_1-C_6)$-alkyl, O—CO—$(C_1-C_6)$-aryl, O—CO—$(C_1-C_6)$-heterocycle; $PO_3H_2$, $SO_3H$, $SO_2$—$NH_2$, $SO_2NH(C_1-C_6)$-alkyl, $SO_2N[(C_1-C_6)$-alkyl]$_2$, S—$(C_1-C_6)$-alkyl, S—$(CH_2)_n$-aryl, S—$(CH_2)_n$-heterocycle, SO—$(C_1-C_6)$-alkyl, SO—$(CH_2)_n$-aryl, SO—$(CH_2)_n$-heterocycle, $SO_2$—$(C_1-C_6)$-alkyl, $SO_2$—$(CH_2)_n$-aryl, $SO_2$—$(CH_2)_n$-heterocycle, $SO_2$—NH$(CH_2)_n$-aryl, $SO_2$—NH$(CH_2)_n$-heterocycle, $SO_2$—N$(C_1-C_6)$-alkyl)$(CH_2)_n$-aryl, $SO_2$—N$(C_1-C_6)$-alkyl)$(CH_2)_n$-heterocycle, $SO_2$—N$((CH_2)_n$-aryl)$_2$, $SO_2$—N$((CH_2)_n$-(heterocycle)$_2$ where n may be 0-6, and the aryl substituent or heterocyclic substituent may be substituted up to twice by F, Cl, Br, OH, $CF_3$, $NO_2$, CN, $OCF_3$, O—$(C_1-C_6)$-alkyl, $(C_1-C_6)$-alkyl, $NH_2$;
C(NH)($NH_2$), $NH_2$, NH—$(C_1-C_6)$-alkyl, $N((C_1-C_6)$-alkyl$)_2$, $NH(C_1-C_7)$-acyl, NH—CO—$(C_1-C_6)$-alkyl, NH—COO—$(C_1-C_6)$-alkyl, NH—CO-aryl, NH—CO-heterocycle, NH—COO-aryl, NH—COO-heterocycle, NH—CO—NH—$(C_1-C_6)$-alkyl, NH—CO—NH-aryl, NH—CO—NH-heterocycle, $N(C_1-C_6)$-alkyl —CO—$(C_1-C_6)$-alkyl, $N(C_1-C_6)$-alkyl —COO—$(C_1-C_6)$-alkyl, $N(C_1-C_6)$-alkyl —CO-aryl, $N(C_1-C_6)$-alkyl —CO-heterocycle, $N(C_1-C_6)$-alkyl —COO-aryl, $N(C_1-C_6)$-alkyl —COO-heterocycle, $N(C_1-C_6)$-alkyl —CO—NH—$(C_1-C_6)$-alkyl), $N(C_1-C_6)$-alkyl —CO—NH-aryl, $N(C_1-C_6)$-alkyl —CO—NH-heterocycle, $N((C_1-C_6)$-alkyl)-CO—N—$(C_1-C_6)$-alkyl$)_2$, $N((C_1-C_6)$-alkyl)-CO—N($(C_1-C_6)$-alkyl)-aryl, $N((C_1-C_6)$-alkyl)-CO—N($(C_1-C_6)$-alkyl)-heterocycle, $N((C_1-C_6)$-alkyl)-CO—N-(aryl)$_2$, $N((C_1-C_6)$-alkyl)-CO—N-(heterocycle)$_2$, N(aryl)-CO—$(C_1-C_6)$-alkyl, N(heterocycle)-CO—$(C_1-C_6)$-alkyl, N(aryl)-COO—$(C_1-C_6)$-alkyl, N(heterocycle)-COO—$(C_1-C_6)$-alkyl, N(aryl)-CO-aryl, N(heterocycle)-CO-aryl, N(aryl)-COO-aryl, N(heterocycle)-COO-aryl, N(aryl)-CO—NH—$(C_1-C_6)$-alkyl), N(heterocycle)-CO—NH—$(C_1-C_6)$-alkyl), N(aryl)-CO—NH-aryl, N(heterocycle)-CO—NH-aryl, N(aryl)-CO—N—$(C_1-C_6)$-alkyl$)_2$, N(heterocycle)-CO—N—$(C_1-C_6)$-alkyl$)_2$, N(aryl)-CO—N($(C_1-C_6)$-alkyl)-aryl, N(heterocycle)-CO—N($(C_1-C_6)$-alkyl)-aryl, N(aryl)-CO—N-(aryl)$_2$, N(heterocycle)-CO—N-(aryl)$_2$, aryl, O—$(CH_2)_n$-aryl, O—$(CH_2)_n$-heterocycle, where n may be 0-6, where the aryl substituent or heterocyclic substituent may be substituted one to 3 times by F, Cl, Br, I, OH, $CF_3$, $NO_2$, CN, $OCF_3$, O—$(C_1-C_6)$-alkyl, $(C_1-C_6)$-alkyl, $NH_2$, $NH(C_1-C_6)$-alkyl, $N((C_1-C_6)$-alkyl$)_2$, $SO_2$—$CH_3$, COOH, COO—$(C_1-C_6)$-alkyl, $CONH_2$.

Heterocycle or heterocyclic substituent means rings and ring systems which, apart from carbon, also comprise heteroatoms such as, for example, nitrogen, oxygen or sulfur. Also included in this definition are ring systems in which the heterocycle or the heterocyclic substituent is fused to benzene nuclei.

Suitable heterocyclic rings, heterocycle or heterocyclic substituents are acridinyl, azocinyl, benzimidazolyl, benzofuryl, benzothienyl, benzothiophenyl, benzoxazolyl, benzthiazolyl, benztriazolyl, benztetrazolyl, benzisoxazolyl, benzisothiazolyl, benzimidazalinyl, carbazolyl, 4aH-carbazolyl, carbolinyl, quinazolinyl, quinolinyl, 4H-quinolizinyl, quinoxalinyl, quinuclidinyl, chromanyl, chromenyl, cinnolinyl, decahydroquinolinyl, 2H,6H-1,5,2-dithiazinyl, dihydrofuro [2,3-b]-tetrahydrofuran, furyl furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl (benzimidazolyl), isothiazolyl, isoxazolyl, morpholinyl, naphthyridinyl, octahydroisoquinolinyl, oxadiazolyl, 1,2,3-oxadiazolyl, 1,2, 4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purynyl, pyranyl, pyrazinyl, pyroazolidinyl, pyrazolinyl, pyrazolyl, pyridazinyl, pyridooxazoles, pyridoimidazoles, pyridothiazoles, pyridinyl, pyridyl, pyrimidinyl, pyrrolidinyl, pyrrolinyl, 2H-pyrrolyl, pyrrolyl, tetrahydrofuranyl, tetrahydroisoquinolinyl, tetrahydroquinolinyl, 6H-1,2,5-thiadazinyl, thiazolyl, 1,2,3-thiadiazolyl, 1,2, 4-thiadiazolyl, 1,2,5-thiadiazolyl, 1,3,4-thiadiazolyl, thienyl, triazolyl, tetrazolyl and xanthenyl.

Pyridyl stands both for 2-, 3- and 4-pyridyl. Thienyl stands both for 2- and 3-thienyl. Furyl stands both for 2- and 3-furyl.

Also included are the corresponding N-oxides of these compounds, that is to say, for example, 1-oxy-2-, 3- or 4-pyridyl.

Also included are derivatives of these heterocycles which are benzo-fused one or more times.

The heterocyclic rings, heterocycle or heterocyclic substituents may be substituted one or more times by suitable groups such as, for example: F, Cl, Br, I, $CF_3$, $NO_2$, $N_3$, CN, COOH, COO($C_1$-$C_6$)alkyl, $CONH_2$, CONH($C_1$-$C_6$)alkyl, CON[($C_1$-$C_6$)alkyl]$_2$, cycloalkyl, ($C_1$-$C_{10}$)-alkyl, ($C_2$-$C_6$)-alkenyl, ($C_2$-$C_6$)-alkynyl, O—($C_1$-$C_6$)-alkyl O—CO—($C_1$-$C_6$)-alkyl, O—CO—($C_1$-$C_6$)-aryl, O—CO—($C_1$-$C_6$)-heterocycle;

$PO_3H_2$, $SO_3H$, $SO_2$—$NH_2$, $SO_2NH(C_1$-$C_6)$-alkyl, $SO_2N[(C_1$-$C_6)$-alkyl]$_2$, S—($C_1$-$C_6$)-alkyl, S—$(CH_2)_n$-aryl, S—$(CH_2)_n$-heterocycle, SO—($C_1$-$C_6$)-alkyl, SO—$(CH_2)_n$-aryl, SO—$(CH_2)_n$-heterocycle, $SO_2$—($C_1$-$C_6$)-alkyl, $SO_2$—$(CH_2)_n$-aryl, $SO_2$—$(CH_2)_n$-heterocycle, $SO_2$—$NH(CH_2)_n$-aryl, $SO_2$—$NH(CH_2)_n$-heterocycle, $SO_2$—$N(C_1$-$C_6)$-alkyl$(CH_2)_n$-aryl, $SO_2$—$N(C_1$-$C_6)$-alkyl$(CH_2)_n$-heterocycle, $SO_2$—$N((CH_2)_n$-aryl$)_2$, $SO_2$—$N((CH_2)_n$-(heterocycle)$_2$ where n may be 0-6, and the aryl substituent or heterocyclic substituent may be substituted up to twice by F, Cl, Br, OH, $CF_3$, $NO_2$, CN, $OCF_3$, O—($C_1$-$C_6$)-alkyl, ($C_1$-$C_6$)-alkyl, $NH_2$;

$C(NH)(NH_2)$, $NH_2$, NH—($C_1$-$C_6$)-alkyl, $N((C_1$-$C_6)$-alkyl)$_2$, $NH(C_1$-$C_7)$-acyl, NH—CO—($C_1$-$C_6$)-alkyl, NH—COO—($C_1$-$C_6$)-alkyl, NH—CO-aryl, NH—CO-heterocycle, NH—COO-aryl, NH—COO-heterocycle, NH—CO—NH—($C_1$-$C_6$)-alkyl, NH—CO—NH-aryl, NH—CO—NH-heterocycle, $N(C_1$-$C_6)$-alkyl —CO—($C_1$-$C_6$)-alkyl, $N(C_1$-$C_6)$-alkyl —COO—($C_1$-$C_6$)-alkyl, $N(C_1$-$C_6)$-alkyl —CO-aryl, $N(C_1$-$C_6)$-alkyl —CO-heterocycle, $N(C_1$-$C_6)$-alkyl —COO-aryl, $N(C_1$-$C_6)$-alkyl —COO-heterocycle, $N(C_1$-$C_6)$-alkyl —CO—NH—($C_1$-$C_6$)-alkyl), $N(C_1$-$C_6)$-alkyl —CO—NH-aryl, $N(C_1$-$C_6)$-alkyl —CO—NH-heterocycle, $N((C_1$-$C_6)$-alkyl)-CO—N—($C_1$-$C_6$)-alkyl)$_2$, $N((C_1$-$C_6)$-alkyl)-CO—N(($C_1$-$C_6)$-alkyl)-aryl, $N((C_1$-$C_6)$-alkyl)-CO—N(($C_1$-$C_6)$-alkyl)-heterocycle, $N((C_1$-$C_6)$-alkyl)-CO—N-(aryl)$_2$, $N((C_1$-$C_6)$-alkyl)-CO—N-(heterocycle)$_2$, N(aryl)-CO—($C_1$-$C_6$)-alkyl, N(heterocycle)-CO—($C_1$-$C_6$)-alkyl, N(aryl)-COO—($C_1$-$C_6$)-alkyl, N(heterocycle)-COO—($C_1$-$C_6$)-alkyl, N(aryl)-CO-aryl, N(heterocycle)-CO-aryl, N(aryl)-COO-aryl, N(heterocycle)-COO-aryl, N(aryl)-CO—NH—($C_1$-$C_6$)-alkyl), N(heterocycle)-CO—NH—($C_1$-$C_6$)-alkyl), N(aryl)-CO—NH-aryl, N(heterocycle)-CO—NH-aryl, N(aryl)-CO—N—($C_1$-$C_6$)-alkyl)$_2$, N(heterocycle)-CO—N—($C_1$-$C_6$)-alkyl)$_2$, N(aryl)-CO—N(($C_1$-$C_6)$-alkyl)-aryl, N(heterocycle)-CO—N(($C_1$-$C_6)$-alkyl)-aryl, N(aryl)-CO—N-(aryl)$_2$, N(heterocycle)-CO—N-(aryl)$_2$, aryl, O—$(CH_2)_n$-aryl, O—$(CH_2)_n$-heterocycle, where n may be 0-6, where the aryl substituent or heterocyclic substituent may be substituted one to 3 times by F, Cl, Br, I, OH, $CF_3$, $NO_2$, CN, $OCF_3$, O—($C_1$-$C_6$)-alkyl, ($C_1$-$C_6$)-alkyl, $NH_2$, $NH(C_1$-$C_6)$-alkyl, $N((C_1$-$C_6)$-alkyl)$_2$, $SO_2$—$CH_3$, COOH, COO—($C_1$-$C_6$)-alkyl, $CONH_2$.

The compounds of the formula I comprise at least two centers of asymmetry and may optionally comprise more in addition thereto. The compounds of the formula I may therefore be in the form of their racemates, racemic mixtures, pure enantiomers, diastereomers and diastereomeric mixtures. The present invention includes all these isomeric forms of the compounds of the formula I. These isomeric forms can be obtained and isolated if necessary by well known methods in the art.

Pharmaceutically acceptable salts of the claimed compounds are particularly suitable for medical applications because their solubility in water is greater than that of the initial or basic compounds. These salts must have a pharmaceutically acceptable anion or cation. Suitable pharmaceutically acceptable acid addition salts of the compounds of the invention are salts of inorganic acids such as hydrochloric acid, hydrobromic, phosphoric, metaphosphoric, nitric and sulfuric acid, and of organic acids such as, for example, acetic acid, benzenesulfonic, benzoic, citric, ethanesulfonic, fumaric, gluconic, glycolic, isethionic, lactic, lactobionic, maleic, malic, methanesulfonic, succinic, p-toluenesulfonic and tartaric acid. Suitable pharmaceutically acceptable basic salts are ammonium salts, alkali metal salts (such as sodium and potassium salts), alkaline earth metal salts (such as magnesium and calcium salts), trometamol (2-amino-2-hydroxymethyl-1,3-propanediol), diethanolamine, lysine or ethylenediamine.

Even those salts with a pharmaceutically unacceptable anion such as, for example, trifluoroacetate, however, also fall within the scope of the present invention since these may also be useful intermediates for the preparation or purification of pharmaceutically acceptable salts and/or for use in non-therapeutic in vitro applications.

The term "physiologically functional derivative" as used herein refers to any physiologically suitable derivative of a compound of formula I of the invention, such as an ester, which on administration to a mammal such as a human is able to form (directly or indirectly) a compound of the formula I or an active metabolite thereof.

Physiologically functional derivatives also include prodrugs of the compounds of the invention, as described, for example, in H. Okada et al., Chem. Pharm. Bull. 1994, 42, 57-61. Such pro-drugs can be metabolized in vivo to a compound of the invention. These pro-drugs may themselves be active or not.

The compounds of the invention may also exist in various polymorphous forms, for example as amorphous and crystalline polymorphous forms. All polymorphous forms of the compounds of the invention belong within the framework of the invention and are a further aspect of the invention.

All references to "compound(s) of formula I" hereinafter refer to compound(s) comprising 8-aminoalkoxy xanthines derivatives of formula I as described above, a salt, solvate and functional derivative thereof as described herein.

PPARdelta compounds which are encoded by different genes (see *Peroxisome Proliferator-Activated Receptor (PPAR): Structure, Mechanisms of Activation and Diverse Functions:* Motojima K, Cell Struct Funct., 1993 October, 18(5), 267-77). which is hereby incorporated by reference.

Two variants of PPARgamma exist, PPARgamma$_1$ and gamma$_2$, which are the result of an alternative use of the promoters and differential mRNA splicing (Vidal-Puig et al. J. Clin. Invest., 97:2553-2561, 1996). Different PPAR receptors have different tissue distribution and modulate different physiological functions. The PPAR receptors play a key role in various aspects of the regulation of a Compounds of this type are particularly suitable for the treatment and/or prevention of Disorders of fatty acid metabolism and glucose utilization disorders Disorders in which insulin resistance is involved Diabetes mellitus, especially type-2 diabetes, including the prevention of the disease manifestations associated therewith.

Particular metabolic states/results achievable by treatment using compounds/compositions of the present invention include, but are not limited to:

hyperglycemia, improvement in insulin resistance, improvement in glucose tolerance, protection of the pancreatic β cells prevention of macro- and microvascular disorders Other metabolic disorders and their associated disease states suitable for the treatment and/or prevention resulting therefrom include:

A. Dyslipidemias and the disease states resulting therefrom such as, for example, atherosclerosis, coronary heart disease, cerebrovascular disorders etc, especially those (but not restricted thereto) which are characterized by one or more of the following factors:
high plasma triglyceride concentrations, high postprandial plasma triglyceride concentrations,
low HDL cholesterol concentration
low ApoA lipoprotein concentrations
high LDL cholesterol concentrations
small dense LDL cholesterol particles
high ApoB lipoprotein concentrations B. Various other conditions which may be associated with the metabolic syndrome, such as:
obesity (excess weight), including central obesity
thromboses, hypercoagulable and prothrombotic stages (arterial and venous)
high blood pressure
heart failure such as, for example (but not restricted thereto), following myocardial infarction, hypertensive heart disease or cardiomyopathy C. Further disorders or conditions in which for example inflammatory reactions or cell differentiation are involved:
atherosclerosis such as, for example (but not restricted thereto), coronary sclerosis including angina pectoris or myocardial infarction, stroke
vascular restenosis or re-occlusion
chronic inflammatory bowel diseases such as, for example, Crohn's disease and ulcerative colitis
pancreatitis
other inflammatory states
retinopathy
adipose cell tumors
lipomatous carcinomas such as, for example, liposarcomas
solid tumors and neoplasms such as, for example (but not restricted thereto), carcinomas of the gastrointestinal tract, of the liver, of the biliary tract and of the pancreas, endocrine tumors, carcinomas of the lungs, of the kidneys and the urinary tract, of the genital tract, prostate carcinomas etc.
acute and chronic myeloproliferative disorders and lymphomas
angiogenesis
neurodegenerative disorders
Alzheimer's disease
multiple sclerosis
Parkinson's disease
erythemato-squamous dermatoses such as, for example, psoriasis
acne vulgaris
other skin disorders and dermatological conditions which are modulated by PPAR
eczemas and neurodermatitis
dermatitis such as, for example, seborrheic dermatitis or photodermatitis
keratitis and keratoses such as, for example, seborrheic keratoses, senile keratoses, actinic keratosis, photo-induced keratoses or keratosis follicularis
keloids and keloid prophylaxis
warts, including condylomata or condylomata acuminata
human papilloma viral (HPV) infections such as, for example, venereal warts, viral warts such as, for example, molluscum contagiosum, leukoplakia
papular dermatoses such as, for example, lichen planus
skin cancer such as, for example, basal-cell carcinomas, melanomas or cutaneous T-cell lymphomas
localized benign epidermal tumors such as, for example, keratoderma, epidermal naevi
chilblains
high blood pressure
syndrome X
polycystic ovary syndrome (PCOS)
asthma
osteoarthritis
lupus erythematosus (LE) or inflammatory rheumatic disorders such as, for example, rheumatoid arthritis
vasculitis
wasting (cachexia)
gout
ischemia/reperfusion syndrome
acute respiratory distress syndrome (ARDS)

The amount of a compound of formula I necessary to achieve the desired biological effect depends on a number of factors, for example, the specific compound chosen, the intended use, the mode of administration and the clinical condition of the patient. The daily dose is generally in the range from 0.001 mg to 100 mg (typically of 0.01 mg and 50 mg) per day and per kilogram of bodyweight, for example 0.1-10 mg/kg/day. An intravenous dose may be, for example, in the range from 0.001 mg to 1.0 mg/kg, which can suitably be administered as infusion of 10 ng to 100 ng per kilogram and per minute. Suitable infusion solutions for these purposes may contain, for example, from 0.1 ng to 10 mg, typically from 1 ng to 10 mg, per milliliter. Single doses may contain, for example, from 1 mg to 10 g of the active ingredient. Thus, ampoules for injections may contain, for example, from 1 mg to 100 mg, and single-dose formulations which can be administered orally, such as, for example, capsules or tablets, may contain, for example, from 0.05 to 1000 mg, typically from 0.5 to 600 mg. For the therapy of the above-mentioned conditions, the compounds of formula I may be used as the compound itself, but they are preferably in the form of a pharmaceutical composition with an acceptable carrier. The carrier must, of course, be acceptable in the sense that it is compatible with the other ingredients of the composition and is not harmful to the patient's health. The carrier may be a solid or a liquid or both and is preferably formulated with the compound as a single dose, for example as a tablet, which may contain from 0.05% to 95% by weight of the active ingredient. Other pharmaceutically active substances may likewise be present, including other compounds of formula I. The pharmaceutical compositions of the invention can be produced by one of the known pharmaceutical methods, which essentially consist of mixing the ingredients with pharmacologically acceptable carriers and/or excipients.

Pharmaceutical compositions of the invention are those suitable for oral, rectal, topical, peroral, i.e., sublingual and parenteral i. e., subcutaneous, intramuscular, intradermal or intravenous, administration, although the most suitable mode of administration depends in each individual case on the nature and severity of the condition to be treated and on the nature of the compound of formula I used in each case. Coated formulations and coated slow-release formulations also belong within the framework of the invention. Preference is given to acid- and gastric juice-resistant formulations. Suitable coatings resistant to gastric juice comprise cellulose acetate phthalate, polyvinyl acetate (PVA) phthalate, hydroxypropyl methylcellulose (HPMC) phthalate and anionic polymers of methacrylic acid and methyl methacrylate.

Suitable pharmaceutical preparations for oral administration may be in the form of separate units such as, for example, capsules, cachets, slow-dissolving oral tablets, each of which contain a defined amount of the compound of formula I; as powders or granules, as solution or suspension in an aqueous or non-aqueous liquid; or as an oil-in-water or water-in-oil emulsion. These compositions may, as already mentioned, be prepared by any suitable pharmaceutical method which includes a step in which the active ingredient and the carrier (which may consist of one or more additional ingredients) are brought into contact. The compositions are generally produced by uniform and homogeneous mixing of the active ingredient with a liquid and/or finely divided solid carrier, after which the product is shaped if necessary. Thus, for example, a tablet can be produced by compressing or molding a powder or granules of the compound, where appropriate with one or more additional ingredients. Compressed tablets can be produced by tableting the compound in free-flowing form such as, for example, a powder or granules, where appropriate mixed with a binder, glidant, inert diluent and/or one (or more) surface-active/dispersing agents in a suitable machine. Molded tablets can be produced by molding the compound, which is in powder form and is moistened with an inert liquid diluent, in a suitable machine.

Pharmaceutical compositions which are suitable for peroral (sublingual) administration comprise slow-dissolving, oral tablets which contain a compound of formula I with a flavoring, normally sucrose and gum arabic or tragacanth, and pastilles which comprise the compound in an inert base such as gelatin and glycerol or sucrose and gum arabic.

Pharmaceutical compositions suitable for parenteral administration comprise preferably sterile aqueous preparations of a compound of formula I, which are preferably isotonic with the blood of the intended recipient. These preparations are preferably administered intravenously, although administration may also take place by subcutaneous, intramuscular or intradermal injection. These preparations can preferably be produced by mixing the compound with water and making the resulting solution sterile and isotonic with blood. Injectable compositions of the invention generally contain from 0.1 to 5.0% by weight of the active compound.

Pharmaceutical compositions suitable for rectal administration are preferably in the form of single-dose suppositories. These can be produced by mixing a compound of the formula I with one or more conventional solid carriers, for example cocoa butter, and shaping the resulting mixture.

Pharmaceutical compositions suitable for topical use on the skin are preferably in the form of ointment, cream, lotion, paste, spray, aerosol or oil. Carriers which can be used are petrolatum, lanolin, polyethylene glycols, alcohols and combinations of two or more of these substances. The active ingredient is generally present in a concentration of from 0.1 to 15% by weight of the composition, for example from 0.5 to 2%.

Transdermal administration is also possible. Pharmaceutical compositions suitable for transdermal uses can be in the form of single plasters which are suitable for long-term close contact with the patient's epidermis. Such plasters suitably contain the active ingredient in an aqueous solution which is buffered where appropriate, dissolved and/or dispersed in an adhesive or dispersed in a polymer. A suitable active ingredient concentration is about 1% to 35%, preferably about 3% to 15%. A particular possibility is for the active ingredient to be released by electro-transport or iontophoresis as described, for example, in Pharmaceutical Research, 2(6): 318 (1986) which is also hereby incorporated by reference.

The compounds of the formula I are distinguished by favorable effects on metabolic disorders. They beneficially influence lipid and sugar metabolism, in particular they lower the triglyceride level and are suitable for the prevention and treatment of type II diabetes and arteriosclerosis and the diverse disease conditions which are a result thereof.

The compounds of the present invention according to formula I can be administered alone or optionally in combination with one or more secondary pharmacologically active substances which are effective in the treatment of metabolic disturbances or disorders frequently associated therewith. Examples of such additional active compounds are:

1. active compounds which lower blood glucose, i.e., anti-diabetic agents,
2. active ingredients for the treatment of dyslipidemias,
3. anti-atherosclerotic compounds
4. anti-obesity agents,
5. anti-inflammatory active compounds
6. active compounds for the treatment of malignant tumors
7. anti-thrombotic active compounds
8. active compounds for the treatment of high blood pressure
9. active compounds for the treatment of heart failure and
10. active compounds for the treatment and/or prevention of complications caused by diabetes or associated with diabetes.

These compounds can be combined with the compounds of the invention of formula I resulting in a synergistic enhancement or improvement in the therapeutic effect. Administration of the active ingredient combination can take place either by separate administration of the active ingredients to the patient or in the form of combination products in which a plurality of active ingredients are present in one pharmaceutical preparation. Specific examples of the additional active compounds suitable for combination with those of the present invention include, but are not limited to:

1. Anti-diabetic Agents

Suitable antidiabetic agents are disclosed in the Rote Liste 2001, chapter 12 or in the USP Dictionary of USAN and International Drug Names, US Pharmacopeia, Rockville 2003. Suitable anti-diabetic agents include all insulins and insulin derivatives such as, for example, Lantus® (see www.lantus.com) or Apidra®, and other fast-acting insulins (see U.S. Pat. No. 6,221,633 to Ertle et. al.), GLP-1 receptor modulators as described in WO 01/04146 or else, for example, those disclosed in U.S. Pat. No. 6,268,343 to Knudsen et. al. (Novo Nordisk A/S) both of which are incorporated by reference herein The orally effective hypoglycemic active ingredients include, preferably, sulfonylureas, biguanidines, meglitinides, oxadiazolidinediones, thiazolidinediones, glucosidase inhibitors, glucagon antagonists, oral GLP-1 agonists, DPP-IV inhibitors, potassium channel openers such as, for example, those disclosed in U.S. Pat. No. 5,889,002 and U.S. Pat. No. 6,225,310 both to Nielsen et. al., insulin sensitizers, inhibitors of liver enzymes involved in the stimulation of gluconeogenesis and/or glycogenolysis, modulators of glucose uptake, compounds which alter lipid metabolism and lead to a change in the blood lipid composition, compounds which reduce food intake or food absorption, PPAR and PXR modulators and active ingredients which act on the ATP-dependent potassium channel of the beta cells.

In one embodiment of the invention, the compounds of the formula I are administered in combination with insulin.

In one embodiment of the invention, the compounds of the formula I are in combination with substances which influence hepatic glucose production such as, for example, glycogen phosphorylase inhibitors (see: WO 01/94300, WO 02/096864, WO 03/084923, WO 03/084922, WO 03/104188).

In another embodiment, the compounds of the formula I are administered in combination with a sulfonylurea such as, for example, tolbutamide, glibenclamide, glipizide or glimepiride.

In a third embodiment, the compounds of the formula I are administered in combination with an active ingredient which acts on the ATP-dependent potassium channel of the beta cells, such as, for example, tolbutamide, glibenclamide, glipizide, glimepiride or repaglinide.

In yet another embodiment, the compounds of the formula I are administered in combination with a biguanide such as, for example, metformin.

In a further embodiment, the compounds of the formula I are administered in combination with a meglitinide such as, for example, repaglinide.

The compounds of the formula I may also be administered in combination with a thiazolidinedione such as, for example, ciglitazone, pioglitazone, rosiglitazone or the compounds disclosed in WO 97/41097 of Dr. Reddy's Research Foundation, in particular 5-[[4-[(3,4-dihydro-3-methyl-4-oxo-2-quinazolinylmethoxy]phenyl]methyl]-2,4-thiazolidinedione.

In one embodiment of the invention, the compounds of the formula I are administered in combination with a PPAR-gamma agonist such as, for example, rosiglitazone or pioglitazone.

In one embodiment, the compounds of the formula I are administered in combination with compounds with an inhibitory effect on SGLT-1 and/or 2, as disclosed directly or indirectly for example in WO 2004/007517, WO 2004/052902 and WO 2004/052903.

In another embodiment, the compounds of the formula I are administered in combination with an α-glucosidase inhibitor such as, for example, miglitol or acarbose.

In one embodiment, the compounds of the formula I are administered in combination with more than one of the aforementioned compounds, e.g. in combination with a sulfonylurea and metformin, a sulfonylurea and acarbose, repaglinide and metformin, insulin and a sulfonylurea, insulin and metformin, insulin and troglitazone, insulin and lovastatin, etc.

Lipid Modulators

In one embodiment of the invention, the compounds of the formula I are administered in combination with an HMGCoA reductase inhibitor such as lovastatin, fluvastatin, pravastatin, simvastatin, ivastatin, itavastatin, atorvastatin and/or rosuvastatin.

In one embodiment of the invention, the compounds of the formula I are administered in combination with a bile acid absorption inhibitor (see, for example, U.S. Pat. Nos. 6,245, 744; 6,221,897 and 6,277,831 all to Frick et al, EP 0683 773, EP 0683 774).

In one embodiment of the invention, the compounds of the formula I are administered in combination with a polymeric bile acid adsorbent such as, for example, cholestyramine or colesevelam.

In one embodiment of the invention, the compounds of the formula I are administered in combination with a cholesterol absorption inhibitor as described for example in WO 0250027, or ezetimibe, tiqueside and, pamaqueside.

In one embodiment of the invention, the compounds of the formula I are administered in combination with an LDL receptor inducer (see, for example, U.S. Pat. No. 6,342,512 to Kirsch et al.).

In one embodiment, the compounds of the formula I are administered in combination with bulking agents, preferably insoluble bulking agents (see, for example, carob/Caromax® (Zunft H J; et al., Carob pulp preparation for treatment of hypercholesterolemia, ADVANCES IN THERAPY (2001 September-October), 18(5), 230-6). Caromax is a carob-containing product from Nutrinova, Nutrition Specialties & Food Ingredients GmbH, Industriepark Höchst, 65926 Frankfurt/Main)). Combination with Caromax® is possible in one preparation or by separate administration of compounds of the formula I and Caromax®. Caromax® can in this connection also be administered in the form of food products such as, for example, in bakery products or muesli bars.

In one embodiment of the invention, the compounds of the formula I are administered in combination with a PPARalpha agonist, such as, for example, rosiglitazone and pioglitazone, JTT-501, GI 262570.

In one embodiment of the invention, the compounds of the formula I are administered in combination with a PPAR alpha agonist, such as, for example, GW 9578, GW 7647.

In one embodiment of the invention, the compounds of the formula I are administered in combination with a mixed PPAR alpha/gamma agonist, such as, for example, GW 1536, AVE 8042, AVE 8134, AVE 0847, or as described in PCT/US 2000/11833, PCT/US 2000/11490, DE10142734.4.

In one embodiment of the invention, the compounds of the formula I are administered in combination with a mixed PPAR alpha/gamma agonist such as, for example, AZ 242 (Tesaglitazar, (S)-3-(4-[2-(4-methanesulfonyloxyphenyl) ethoxy]phenyl)-2-ethoxypropionic acid), BMS 298585 (N-[(4-methoxyphenoxy)carbonyl]-N-[[4-[2-(5-methyl-2-phenyl-4-oxazolyl)ethoxy]phenyl]methyl]glycine) or as described in WO 99/62872, WO 99/62871, WO 01/40171, WO 01/40169, WO96/38428, WO 01/81327, WO 01/21602, WO 03/020269, WO 00/64888 or WO 00/64876.

In one embodiment of the invention, the compounds of the formula I are administered in combination with a fibrate such as, for example, fenofibrate, gemfibrozil, clofibrate and, bezafibrate.

In one embodiment of the invention, the compounds of the formula I are administered in combination with nicotinic acid or niacin.

In one embodiment of the invention, the compounds of the formula I are administered in combination with a CETP inhibitor, e.g. CP-529, 414 (torcetrapib).

In one embodiment of the invention, the compounds of the formula I are administered in combination with an ACAT inhibitor.

In one embodiment of the invention, the compounds of the formula I are administered in combination with an MTP inhibitor such as, for example, implitapide.

In one embodiment of the invention, the compounds of the formula I are administered in combination with an anti-oxidant.

In one embodiment of the invention, the compounds of the formula I are administered in combination with a lipoprotein lipase inhibitor.

In one embodiment of the invention, the compounds of the formula I are administered in combination with an ATP citrate lyase inhibitor.

In one embodiment of the invention, the compounds of the formula I are administered in combination with a squalene synthetase inhibitor.

In one embodiment of the invention, the compounds of the formula I are administered in combination with a lipoprotein (a) antagonist.

Anti-Obesity Agents

In one embodiment of the invention, the compounds of the formula I are administered in combination with a lipase inhibitor such as, for example, orlistat.

In another embodiment of the invention, the further active ingredient is fenfluramine or dexfenfluramine.

In another embodiment, the further active ingredient is sibutramine.

In a further embodiment, the compounds of the formula I are administered in combination with CART modulators (see "Cocaine-Amphetamine-Regulated Transcript Influences Energy Metabolism, Anxiety and Gastric Emptying in Mice" Asakawa, A, et al., M.: Hormone and Metabolic Research (2001), 33(9), 554-558), NPY antagonists, e.g. naphthalene-1-sulfonic acid {4-[(4-aminoquinazolin-2-ylamino)methyl]-cyclohexylmethyl}amide hydrochloride (CGP 71683A)), MC4 agonists (e.g. 1-amino-1,2,3,4-tetrahydronaphthalene-2-carboxylic acid [2-(3a-benzyl-2-methyl-3-oxo-2,3,3a,4,6,7-hexahydropyrazolo[4,3-c]pyridin-5-yl)-1-(4-chlorophenyl)-2-oxoethyl]amide; (WO 01/91752)), orexin antagonists (e.g. 1-(2-methylbenzoxazol-6-yl)-3-[1,5]naphthyridin-4-ylurea hydrochloride (SB-334867-A)), H3 agonists (3-cyclohexyl-1-(4,4-dimethyl-1,4,6,7-tetrahydroimidazo-[4,5-c]pyridin-5-yl)propan-1-one oxalic acid salt (WO 00/63208)); TNF agonists, CRF antagonists (e.g. [2-methyl-9-(2,4,6-trimethylphenyl)-9H-1,3,9-triazafluoren-4-yl]dipropylamine (WO 00/66585)), CRF BP antagonists (e.g. urocortin), urocortin agonists, β3 agonists (e.g. 1-(4-chloro-3-methanesulfonylmethylphenyl)-2-[2-(2,3-dimethyl-1H-indol-6-yloxy)ethylamino]-ethanol hydrochloride (WO 01/83451)), MSH (melanocyte-stimulating hormone) agonists, CCK-A agonists (e.g. {2-[4-(4-chloro-2,5-dimethoxyphenyl)-5-(2-cyclohexylethyl)thiazol-2-ylcarbamoyl]-5,7-dimethylindol-1-yl}acetic acid trifluoroacetic acid salt (WO 99/15525)), serotonin reuptake inhibitors (e.g. dexfenfluramine), mixed serotonergic and noradrenergic compounds (e.g. WO 00/71549), 5HT agonists e.g. 1-(3-ethylbenzofuran-7-yl)piperazine oxalic acid salt (WO 01/09111), bombesin agonists, galanin antagonists, growth hormone (e.g. human growth hormone), growth hormone-releasing compounds (6-benzyloxy-1-(2-diisopropylaminoethylcarbamoyl)-3,4-dihydro-1H-isoquinoline-2-carboxylic acid tert-butyl ester (WO 01/85695)), TRH agonists (see, for example, EP 0 462 884), uncoupling protein 2 or 3 modulators, leptin agonists (see, for example, Lee, Daniel W.; Leinung, Matthew C.; Rozhavskaya-Arena, Marina; Grasso, Patricia. Leptin agonists as a potential approach to the treatment of obesity. Drugs of the Future (2001), 26(9), 873-881), DA agonists (Bromocriptine, Doprexin), lipase/amylase inhibitors (e.g. WO 00/40569), PPAR modulators (e.g. WO 00/78312), RXR modulators or TR-β agonists).

In one embodiment of the invention, the secondary active ingredient is leptin.

In one embodiment, the further active ingredient is dexamphetamine, amphetamine, mazindole or phentermine.

In one embodiment, the compounds of the formula I are as administered in combination with medicaments having effects on the coronary circulation and the vascular system, such as, for example, ACE inhibitors (e.g. ramipril), medicaments which act on the angiotensin-renin system, calcium antagonists, beta blockers etc.

In one embodiment, the compounds of the formula I are administered in combination with medicaments having an anti-inflammatory effect.

In one embodiment, the compounds of the formula are administered in combination with pharmaceutical agents which are employed for cancer therapy and cancer prevention.

It will be appreciated that every suitable combination of the compounds of the invention with one or more of the aforementioned compounds and optionally one or more other pharmacologically active substances is regarded as falling within the scope of the claims of the present invention. The examples detailed below are provided to better describe and more specifically set forth the compounds, processes and methods of the present invention. It is to be recognized that they are for illustrative purposes only however, and should not be interpreted as limiting the spirit and scope of the invention as later recited by the claims that follow.

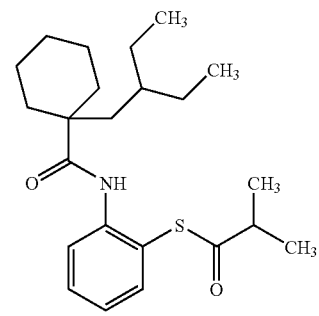

JTT-705

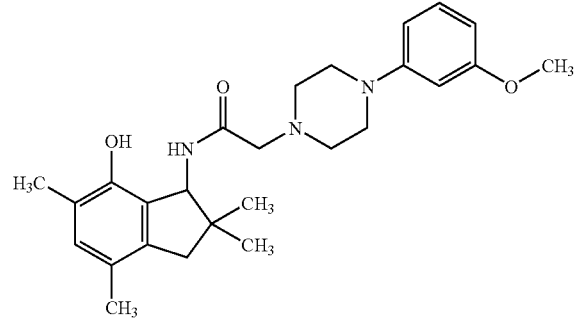

OPC-14117

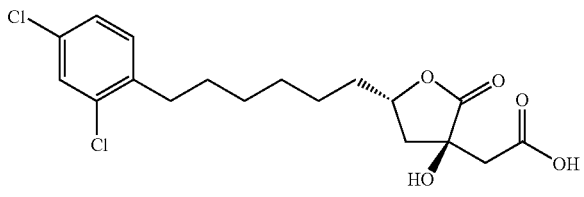

SB-204990

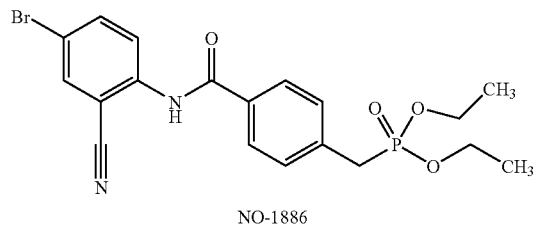

NO-1886

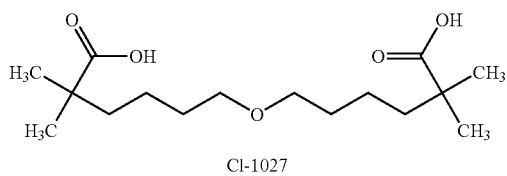

Cl-1027

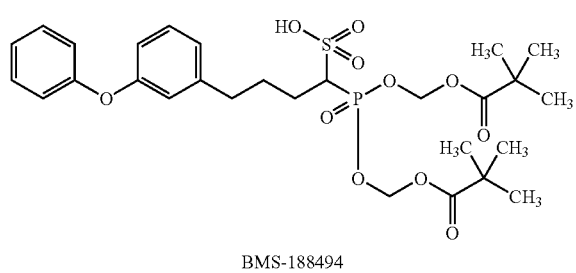

BMS-188494

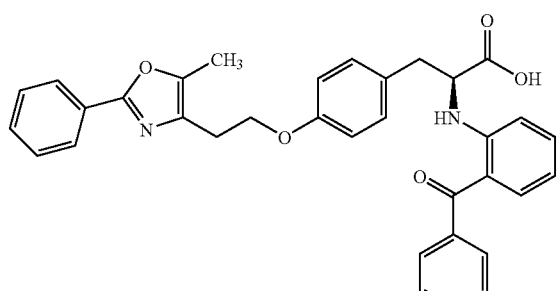

GI 262570

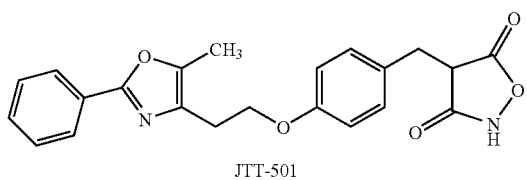

JTT-501

The compounds of the formula I can be The The compounds of the present invention as defined by Formula I can be prepared by reacting suitable starting compounds comprising formula II below in which R1, R2 and R3 have the meaning indicated above, and X is a protection group such as chlorine, bromine, iodine, sulfonyloxy, sulfinyl, sulfoxil, with a compound of the formula III where M is a metal such as lithium, sodium, potassium, cesium, magnesium, calcium etc., where appropriate in the presence of suitable bases in inert solvents to give the compounds of the formula I.

Alternatively, the starting materials of the formula II can be reacted with alcohols of the formula III in which M is hydrogen, in the presence of a suitable base in an inert solvent so as to yield compounds of the present invention as defined by formula I.

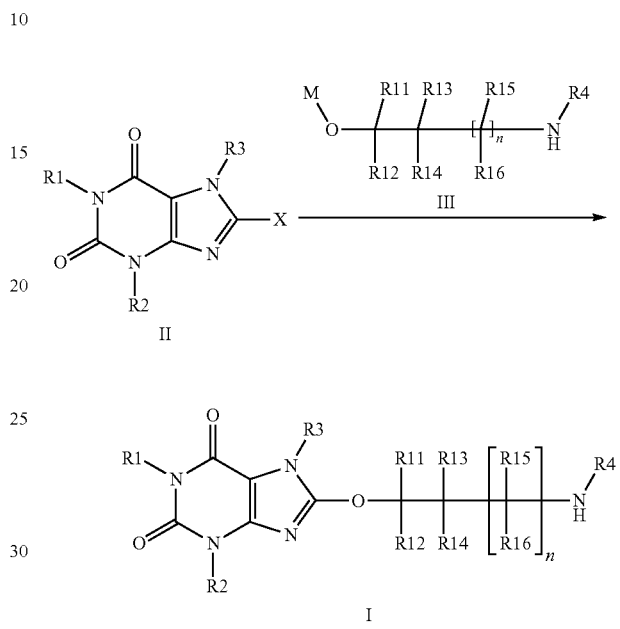

In cases where R4 is hydrogen, it may be expedient to employ the substituent—NHR4 in a form protected on the nitrogen function, and to eliminate the protective group later at a suitable point in the reaction. Such suitable protective groups and methods for introduction and elimination are known (see Theodora W. Greene and Peter G. M. Wuts, Protective Groups in Organic Synthesis, 3rd edition, John Wiley & Sons, Inc., New York, 1999) which is incorporated herein by reference.

The halogen compounds of the formula II can be obtained by known methods such as, for example, by halogenation of the corresponding H or OH compound (formula 2, X=H, OH). Suitable halogenating agents may be by way of example halogens such as chlorine and bromine, N-bromosuccinimide, phosphorus pentoxide or phosphorus oxychloride. Synthesis of compounds of the formula II is also well known in the literature (see Houben Weyl E9b/2, pp. 331 et seq.). The compounds can be produced from diaminopyrimidine derivatives or aminoimidazolecarboxamides by reaction with suitable reagents and be converted into the desired starting compounds of the formula II by targeted chemical modifications such as hydrolysis, alkylation, and/or halogenation.

The substituents R1 to R3 can be prepared by methods known per se, by alkylation of corresponding precursors, it being possible to vary the sequence. However, in some cases they can also be introduced by the selection of appropriate precursors for the preparation of the xanthine structure. The compounds of formula III are known or can be prepared by methods known from the literature.

TABLE 1

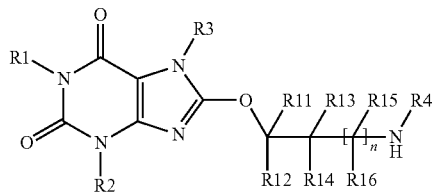

I

| Ex. | R1 | R2 | R3 | R4 | R11 | R12 | R13 | R14 | n | R15 | R16 |
|---|---|---|---|---|---|---|---|---|---|---|---|
| 1 | Ph—CO—CH$_2$— | CH$_3$ | —CH$_2$CH=C(CH$_3$)$_2$ | H | H | H | CH$_3$ | CH$_3$ | 0 | — | — |
| 2 | Ph—CO—CH$_2$— | CH$_3$ | —CH$_2$CH=C(CH$_3$)$_2$ | H | H | H | H | H | 0 | — | — |
| 3 | Ph—CO—CH$_2$— | CH$_3$ | —CH$_2$CH=C(CH$_3$)$_2$ | H | H | H | CH$_2$—Ph—4-Cl | H | 0 | — | — |
| 4 | Ph—CO—CH$_2$— | CH$_3$ | —CH$_2$CH=C(CH$_3$)$_2$ | H | H | H | CH$_3$ | H | 0 | — | — |
| 5 | Ph—CO—CH$_2$— | CH$_3$ | —CH$_2$CH=C(CH$_3$)$_2$ | R$_4$ + R$_{11}$ = (CH$_2$)$_3$ | | H | H | H | 0 | — | — |
| 6 | Ph—CO—CH$_2$— | CH$_3$ | —CH$_2$CH=C(CH$_3$)$_2$ | H | H | H | CH$_3$ | CH$_3$ | 1 | H | H |
| 7 | Ph—CO—CH$_2$— | CH$_3$ | —CH$_2$CH=C(CH$_3$)$_2$ | | H | H | R$_4$ + R$_{13}$ = (CH$_2$)$_3$ | H | 0 | — | — |
| 8 | Ph—CO—CH$_2$— | CH$_3$ | —CH$_2$CH=C(CH$_3$)$_2$ | | H | H | (S)-R$_4$ + R$_{13}$ = (CH$_2$)$_2$ | H | 0 | — | — |
| 9 | Ph—CO—CH$_2$— | CH$_3$ | —CH$_2$CH=C(CH$_3$)$_2$ | | H | H | (S)-R$_4$ + R$_{13}$ = (CH$_2$)$_2$ | H | 1 | H | H |
| 10 | Ph—CO—CH$_2$— | CH$_3$ | —CH$_2$CH=C(CH$_3$)$_2$ | | H | H | (R)-R$_4$ + R$_{13}$ = (CH$_2$)$_2$ | H | 1 | H | H |
| 11 | Ph—CO—CH$_2$— | CH$_3$ | —CH$_2$CH=C(CH$_3$)$_2$ | H | H | H | (R)-CH$_3$ | H | 0 | — | — |
| 12 | Ph—CO—CH$_2$— | CH$_3$ | —CH$_2$CH=C(CH$_3$)$_2$ | H | H | H | H | H | 1 | H | H |
| 13 | Ph—CO—CH$_2$— | CH$_3$ | —CH$_2$CH=C(CH$_3$)$_2$ | H | CH$_3$—HCl | H | H | H | 0 | — | — |
| 14 | Ph—CO—CH$_2$— | CH$_3$ | —CH$_2$CH=C(CH$_3$)$_2$ | H | R$_{11}$ + R$_{13}$ = (CH$_2$)$_4$(trans) | H | H | H | 0 | — | — |
| 15 | Ph—CO—CH$_2$— | CH$_3$ | —CH$_2$CH=C(CH$_3$)$_2$ | H | R$_{11}$ + R$_{13}$ = (CH$_2$)$_4$(cis) | H | H | H | 0 | — | — |
| 16 | Ph—CO—CH$_2$— | CH$_3$ | —CH$_2$(2-Cl,4-F—Ph) | H | H | H | H | H | 0 | — | — |
| 17 | Ph—CO—CH$_2$— | CH$_2$—CH$_3$ | —CH$_2$CH=C(CH$_3$)$_2$ | H | H | H | H | H | 0 | — | — |
| 18 | Ph—CO—CH$_2$— | CH$_3$ | —CH$_2$—CC—CH$_3$ | H | H | H | H | H | 0 | — | — |
| 19 | Ph—CO—CH$_2$— | CH$_3$ | —CH$_2$CH=C(CH$_3$)$_2$ | H | R$_{11}$ + R$_{13}$ = indane-1,2-diyl (1S,2R) | H | H | H | 0 | — | — |
| 20 | Ph—CO—CH$_2$— | CH$_3$ | —CH$_2$CH=C(CH$_3$)$_2$ | H | H | H | CH$_2$—Ph trifluoro-acetate | H | 0 | — | — |
| 21 | Ph—CO—CH$_2$— | CH$_3$ | —CH$_2$CH=C(CH$_3$)$_2$ | H | R$_{11}$ + R$_{13}$ = indane-1,2-diyl (1R,2S) | H | trifluoro-acetate | H | 0 | — | — |
| 22 | CH$_3$ | CH$_3$ | —CH$_2$(2-CN—Ph) | H | H | H | H | H | 0 | — | — |
| 23 | CH$_3$ | CH$_3$ | —CH$_2$CH=CH—Ph | H | H | H | H | H | 0 | — | — |
| 24 | Ph—CO—CH$_2$— | CH$_2$—CF$_3$ | CH$_2$CH=C(CH$_3$)$_2$ | H | H | H | H.HCl | H | 0 | — | — |
| 25 | Ph—CO—CH$_2$— | CH$_3$ | —CH$_2$CH=C(CH$_3$)$_2$ | | H | H | (R)-R$_4$ + R$_{13}$ = (CH$_2$)$_2$ | H | 0 | — | — |
| 26 | Ph—CO—CH$_2$— | CH$_3$ | —CH$_2$CH=C(CH$_3$)$_2$ | (R)-R$_4$ + R$_{11}$ = (CH$_2$)$_2$ | | H | H | H | 0 | — | — |
| 27 | Ph—CO—CH$_2$— | CH$_3$ | —CH$_2$CH=C(CH$_3$)$_2$ | (S)-R$_4$ + R$_{11}$ = (CH$_2$)$_2$ | | H | H | H | 0 | — | — |
| 28 | Ph—CO—CH$_2$— | CH$_3$ | —CH$_2$CH=C(CH$_3$)$_2$ | H | R$_{11}$ + R$_{13}$ = (CH$_2$)$_4$ cis | H | H | H | 1 | H | H |
| 29 | Ph—CO—CH$_2$— | CH$_3$ | —CH$_2$CH=C(CH$_3$)$_2$ | H | H | H | R$_{13}$ + R$_{15}$ = (CH$_2$)$_4$ trans | H | 1 | | H |
| 30 | Ph—CO—CH$_2$— | CH$_3$ | —CH$_2$CH=C(CH$_3$)$_2$ | H | H | H | R$_{13}$ + R$_{15}$ = (CH$_2$)$_4$ cis | H | 1 | | H |
| 31 | Ph—CO—CH$_2$— | CH$_3$ | —CH$_2$CH=C(CH$_3$)$_2$ | H | R$_{11}$ + R$_{13}$ = (CH$_2$)$_3$ trans | H | | H | 0 | — | — |
| 32 | Ph—CO—CH$_2$— | CH$_3$ | —CH$_2$CH=C(CH$_3$)$_2$ | H | R$_{11}$ + R$_{13}$ = (CH$_2$)$_4$ trans | H | hydrochloride | H | 0 | — | — |
| 33 | Ph—OO—CH$_2$— | CH$_3$ | —CH$_2$CH=C(CH$_3$)$_2$ | H | H | H | CH$_{3.HCl}$ | CH$_3$ | 1 | H | H |
| 34 | Ph—CO—CH$_2$— | CH$_3$ | —CH$_2$CH=C(CH$_3$)$_2$ | H | H | H | CH$_3$ | H | 1 | H | H |
| 35 | Ph—CO—CH$_2$— | CH$_3$ | —CH$_2$CH=C(CH$_3$)$_2$ | H | R$_{11}$ + R$_{13}$ = (CH$_2$)$_4$ trans | H | | H | 1 | H | H |

TABLE 1-continued

Structure I: Xanthine core with R1 on N1, R2 on N3, R3 on N7, and at C8 an -O-C(R11)(R12)-C(R13)(R14)-[C(R15)(R16)]n-NH-R4 substituent.

| Ex. | R1 | R2 | R3 | R4 | R11 | R12 | R13 | R14 | n | R15 | R16 |
|---|---|---|---|---|---|---|---|---|---|---|---|
| 36 | Ph—CO—CH$_2$— | CH$_3$ | —CH$_2$CH=C(CH$_3$)$_2$ | H | R$_{11}$ + R$_{13}$ = (CH$_2$)$_4$ trans | H | hydrochloride | H | 1 | H | H |
| 37 | Ph—CO—CH$_2$— | CH$_3$ | —CH$_2$CH=C(CH$_3$)$_2$ | H | R$_{11}$ + R$_{13}$ = (CH$_2$)$_4$ trans | H | diastereomer 1 | H | 1 | H | H |
| 38 | Ph—CO—CH$_2$— | CH$_3$ | —CH$_2$CH=C(CH$_3$)$_2$ | H | R$_{11}$ + R$_{13}$ = (CH$_2$)$_4$ trans | H | diastereomer 2 | H | 1 | H | H |
| 39 | Ph—CO—CH$_2$— | CH$_3$ | —CH$_2$CH=C(CH$_3$)$_2$ | H | R$_{11}$ + R$_{13}$ = (CH$_2$)$_4$ trans | H | hydrochloride diastereomer 1 | H | 0 | — | — |
| 40 | Ph—CO—CH$_2$— | CH$_3$ | —CH$_2$CH=C(CH$_3$)$_2$ | H | R$_{11}$ + R$_{13}$ = (CH$_2$)$_4$ trans | H | hydrochloride diastereomer 2 | H | 0 | — | — |
| 41 | CH$_3$ | CH$_3$ | —CH$_2$—(2-Cl—Ph) | H | R$_{11}$ + R$_{13}$ = (CH$_2$)$_4$ trans | H | | H | 0 | — | — |

The compounds of the formula I are notable for beneficial effects on lipid and carbohydrate metabolism, in particular they lower the blood glucose level and are suitable for the treatment of type 2 diabetes, of insulin resistance, of dyslipidemias and of metabolic syndrome/syndrome X. The compounds are also suitable for the prophylaxis and treatment of arteriosclerotic manifestations. The compounds can be employed alone or in combination with other blood glucose-lowering active ingredients. As discussed above, the compounds act as dipeptidyl peptidase DPP-IV IV) inhibitors and are also suitable for the treatment of disorders of wellbeing and other psychiatric indications such as, for example, depressions, anxiety states, anxiety neuroses, schizophrenia and for the treatment of disorders associated with the circadian rhythm, for weight reduction in mammals, for the treatment of immunological disorders, and for the treatment of drug abuse.

They are also suitable for the treatment of cancer, arthritis, osteoarthritis, osteoporosis, sleep disorders, sleep apnea, female and male sexual disorders, inflammations, acne, pigmentation of the skin, disorders of steroid metabolism, skin diseases, psoriasis, mycoses, neurodegenerative diseases, multiple sclerosis and Alzheimer's disease.

The activity of the compounds was assayed as follows:
Measurement of the DPP-IV activity:
The activity of the compounds was assayed as follows:
Measurement of the DPP-IV activity:
Material:
DPP-IV from porcine kidney (Sigma, Munich)
H-Ala-Pro-AFC (Bachem, Weil am Rhein)
Assay conditions:
DPP-IV (1 mU/ml, final concentration)
H-Ala-Pro-AFC (15 µM, final concentration)
in Tris/HCl (40 mM, pH 7.4), total volume 0.2 ml The reaction was carried out at room temperature for various times (typically 10 min) and stopped at the end of the reaction by adding 20 µl of ZnCl$_2$ (1 M). The H-Ala-Pro-AFC conversion was determined fluorimetrically by measuring the emission at 535 nm after excitation at 405 nm. When inhibitors were added, the added buffer volume was adapted so that a total volume of 200 µl was maintained for the assay mixture. IC50 values for inhibitors were determined by varying the inhibitor concentrations with the stated substrate concentration of 15 µM. Ki and Km values were found by appropriate variation of substrate concentration and inhibitor concentration as described (Dixon, M. and Webb, E. C. (1979) Enzymes, third edition, pp. 47-206, Academic Press). The values for Km, IC50 and Ki were calculated using a commercially available software package (Leatherbarrow, R. J. (1992) GraFit Version 3.0, Erithacus Software Ltd. Staines, U.K.).

TABLE 2

Biological activity

| Examplary embodiment No. | IC-50 (nM) |
|---|---|
| 1 | 92 |
| 2 | 20 |
| 3 | 460 |
| 4 | 28 |
| 7 | 51 |
| 9 | 120 |
| 10 | 34 |
| 11 | 100 |
| 26 | 84 |
| 28 | 13 |
| 37 | 4.5 |

It can be inferred from the table that the compounds of the formula I inhibit the activity of DPP-IV (dipeptidyl peptidase IV) and are thus very suitable for lowering the blood glucose level.

The preparation of some examples is described in detail below, and the other compounds of the formula I were obtained analogously:

EXAMPLE 1

8-(2-Amino-2-methylpropoxy)-3-methyl-7-(3-methylbut-2-enyl)-1-(2-oxo-2-phenylethyl)-3,7-dihydropurine-2,6-dione 15 mg of NaH (50% in liquid paraffin) were added to a solution of 25 mg of 2-amino-2-methylpropan-1-ol in 2 ml of THF (abs), and the mixture was stirred under argon for 30 minutes. Then 100 mg of 8-bromo-3-methyl-7-(3-methylbut-2-enyl)-1-(2-oxo-2-phenylethyl)-3,7-dihydropurine-2,6-dione were added, and the mixture was stirred at room temperature for 15 hours.

After addition of 20 ml of water, the product was extracted with ethyl acetate (2 ×10 ml each time), and the solvent was stripped off in vacuo.

The oily residue was purified by column chromatography (silica gel, mobile phase: methylene chloride: methanol = 9:1).

Yield: 45 mg
m.p.: oil
MS: M+1=440

The following were prepared in a similar fashion using the appropriate amino alcohols:

EXAMPLE 2

8-(2-Aminoethoxy)-3-methyl-7-(3-methylbut-2-enyl)-1-(2-oxo-2-phenylethyl)-3,7-dihydropurine-2,6-dione

MS: M+1=412

EXAMPLE 3

8-[2-Amino-3-(4-chlorophenyl)propoxyl]-3-methyl-7-(3-methylbut-2-enyl)-1-(2-oxo-2-phenylethyl)-3,7-dihydropurine-2,6-dione

MS: M+1=537

EXAMPLE 4

(S)-8-(2-Aminopropoxy)-3-methyl-7-(3-methylbut-2-enyl)-1-(2-oxo-2-phenylethyl)-3,7-dihydropurine-2,6-dione

MS: M+1=426

EXAMPLE 5

3-Methyl-7-(3-methylbut-2-enyl)-1-(2-oxo-2-phenylethyl)-8-(piperidin-3-yloxy)-3,7-dihydropurine-2,6-dione hydrochloride

MS: M+1=452

EXAMPLE 6

8-(3-Amino-2,2-dimethyl-propoxy)-3-methyl-7-(3-methylbut-2-enyl)-1-(2-oxo-2-phenylethyl)-3,7-dihydropurine-2,6-dione

MS: M+1=454

EXAMPLE 7

3-Methyl-7-(3-methylbut-2-enyl)-1-(2-oxo-2-phenylethyl)-8-(piperidin-2-ylmethoxy)-3,7-dihydropurine-2,6-dione

MS: M+1=466

EXAMPLE 8

(S)-3-Methyl-7-(3-methylbut-2-enyl)-1-(2-oxo-2-phenylethyl)-8-(pyrrolidin-2-ylmethoxy)-3,7-dihydropurine-2,6-dione hydrochloride

MS: M+1=452

EXAMPLE 9

(S)-3-Methyl-7-(3-methylbut-2-enyl)-1-(2-oxo-2-phenylethyl)-8-(pyrrolidin-3-ylmethoxy)-3,7-dihydropurine-2,6-dione hydrochloride

MS: M+1=452

EXAMPLE 10

(R)-3-Methyl-7-(3-methylbut-2-enyl)-1-(2-oxo-2-phenylethyl)-8-(pyrrolidin-3-ylmethoxy)-3,7-dihydropurine-2,6-dione hydrochloride

MS: M+1=452

EXAMPLE 11

(R)-8-(2-Aminopropoxy)-3-methyl-7-(3-methylbut-2-enyl)-1-(2-oxo-2-phenylethyl)-3,7-dihydropurine-2,6-dione

MS: M+1=426

EXAMPLE 12

8-(3-Aminopropoxy)-3-methyl-7-(3-methylbut-2-enyl)-1-(2-oxo-2-phenylethyl)-3,7-dihydropurine-2,6-dione

MS: M+1=426

EXAMPLE 13 raz8-(2-Amino-1-methylethoxy)-3-methyl-7-(3-methylbut-2-enyl)-1-(2-oxo-2-phenylethyl)-3,7-dihydropurine-2,6-dione hydrochloride

MS: M+1=426

EXAMPLE 14

8-(trans-2-Aminocyclohexyloxy)-3-methyl-7-(3-methylbut-2-enyl)-1-(2-oxo-2-phenylethyl)-3,7-dihydropurine-2,6-dione

MS: M+1=466

EXAMPLE 15

8-(cis-2-Aminocyclohexyloxy)-3-methyl-7-(3-methylbut-2-enyl)-1-(2-oxo-2-phenylethyl)-3,7-dihydropurine-2,6-dione

MS: M+1=466

EXAMPLE 16

8-(2-Aminoethoxy)-7-(2-chloro-4-fluorobenzyl)-1,3-dimethyl-3,7-dihydropurine-2,6-dione

MS: M+1=382

EXAMPLE 17

8-(2-Aminoethoxy)-3-ethyl-7-(3-methylbut-2-enyl)-1-(2-oxo-2-phenylethyl)-3,7-dihydropurine-2,6-dione

MS: M+1=426

EXAMPLE 18

8-(2-Aminoethoxy)-7-but-2-ynyl-3-methyl-1-(2-oxo-2-phenylethyl)-3,7-dihydropurine-2,6-dione

MS: M+1=396

EXAMPLE 19

1(S)-2(R)-8-(1-Aminoindan-2-yloxy)-3-methyl-7-(3-methylbut-2-enyl)-1-(2-oxo-2-phenylethyl)-3,7-dihydropurine-2,6-dione trifluoroacetate

MS: M+1=500

EXAMPLE 20

8-(2-Amino-3-phenylpropoxy)-3-methyl-7-(3-methylbut-2-enyl)-1-(2-oxo-2-phenylethyl)-3,7-dihydropurine-2,6-dione trifluoroacetate

MS: M+1=502

EXAMPLE 21

1(R)-2(S)-8-(1-Aminoindan-2-yloxy)-3-methyl-7-(3-methylbut-2-enyl)-1-(2-oxo-2-phenylethyl)-3,7-dihydropurine-2,6-dione trifluoroacetate

MS: M+1=500

EXAMPLE 22

2-[8-(2-Aminoethoxy)-1,3-dimethyl-2,6-dioxo-1,2,3,6-tetrahydropurin-7-ylmethyl]benzonitrile

MS: M+1=455

EXAMPLE 23

8-(2-Aminoethoxy)-1,3-dimethyl-7-(3-phenylallyl)-3,7-dihydropurine-2,6-dione

MS: M+1=455

EXAMPLE 24

8-(2-Aminoethoxy)-7-(3-methylbut-2-enyl)-1-(2-oxo-2-phenylethyl)-3-(2,2,2-trifluoroethyl)-3,7-dihydropurine-2,6-dione hydrochloride

MS: M+1=480

EXAMPLE 25

R-3-Methyl-7-(3-methylbut-2-enyl)-1-(2-oxo-2-phenylethyl)-8-(pyrrolidin-2-ylmethoxy)-3,7-dihydropurine-2,6-dione

MS: M+1=452

EXAMPLE 26

R-3-Methyl-7-(3-methylbut-2-enyl)-1-(2-oxo-2-phenylethyl)-8-(pyrrolidin-3-yloxy)-3,7-dihydropurine-2,6-dione

MS: M+1=438

EXAMPLE 27

S-3-Methyl-7-(3-methylbut-2-enyl)-1-(2-oxo-2-phenylethyl)-8-(pyrrolidin-3-yloxy)-3,7-dihydropurine-2,6-dione

MS: M+1=438

EXAMPLE 28 cis-8-(2-Aminomethylcyclohexyloxy)-3-methyl-7-(3-methylbut-2-enyl)-1-(2-oxo-2-phenylethyl)-3,7-dihydropurine-2,6-dione

MS: M+1=480

EXAMPLE 29 trans-8-(2-Aminocyclohexylmethoxy)-3-methyl-7-(3-methylbut-2-enyl)-1-(2-oxo-2-phenylethyl)-3,7-dihydropurine-2,6-dione

MS: M+1=480

EXAMPLE 30 cis-8-(2-Aminocyclohexylmethoxy)-3-methyl-7-(3-methylbut-2-enyl)-1-(2-oxo-2-15 phenylethyl)-3,7-dihydropurine-2,6-dione

MS: M+1=480

EXAMPLE 31 trans-8-(2-Aminocyclopentyloxy)-3-methyl-7-(3-methylbut-2-enyl)-1-(2-oxo-2-phenylethyl)-3,7-dihydropurine-2,6-dione

MS: M+1=452

EXAMPLE 32 trans-8-(2-Aminocyclohexyloxy)-3-methyl-7-(3-methylbut-2-enyl)-1-(2-oxo-2-phenylethyl)-3,7-dihydropurine-2,6-dione hydrochloride

MS: M+1=466

EXAMPLE 33

8-(3-Amino-2,2-dimethylpropoxy)-3-methyl-7-(3-methylbut-2-enyl)-1-(2-oxo-2-phenylethyl)-3,7-dihydropurine-2,6-dione hydrochloride

MS: M+1=454

EXAMPLE 34

3-Methyl-7-(3-methylbut-2-enyl)-1-(2-oxo-2-phenylethyl)-8-(2,2,6,6-tetramethylpiperidin-4-yloxy)-3,7-dihydropurine-2,6-dione

MS: M+1=508

EXAMPLE 35

8-(3-Amino-2-methylpropoxy)-3-methyl-7-(3-methylbut-2-enyl)-1-(2-oxo-2-phenylethyl)-3,7-dihydropurine-2,6-dione

MS: M+1=440

EXAMPLE 36 trans-8-(2-Aminomethylcyclohexyloxy)-3-methyl-7-(3-methylbut-2-enyl)-1-(2-oxo-2-phenylethyl)-3,7-dihydropurine-2,6-dione (mixture of diastereomers)

MS: M+1=480

EXAMPLE 37 trans-8-(2-Aminomethylcyclohexyloxy)-3-methyl-7-(3-methylbut-2-enyl)-1-(2-oxo-2-phenylethyl)-3,7-dihydropurine-2,6-dione hydrochloride (mixture of diastereomers)

MS: M+1=480

EXAMPLE 38 trans-8-(2-Aminomethylcyclohexyloxy)-3-methyl-7-(3-methylbut-2-enyl)-1-(2-oxo-2-phenylethyl)-3,7-dihydropurine-2,6-dione (diastereomer 1)

This compound was obtained as the faster-eluting isomer by chromatographic separation of the mixture of diastereomers (Example 36) on a chiral column (Chiralpak AD 10×40 cm, manufactured by Merck; eluent: methanol+0.1% diethylamine; flow 20 rate: 200 ml/min).
MS: M+1=480
m.p.: 151.7° C.

EXAMPLE 39 trans-8-(2-Aminomethylcyclohexyloxy)-3-methyl-7-(3-methylbut-2-enyl)-1-(2-oxo-2-phenylethyl)-3,7-dihydropurine-2,6-dione (diastereomer 2)

This compound was obtained as the isomer with the longer retention time by chromatographic separation of the mixture of diastereomers (Example 36) on a chiral column (Chiralpak AD 10×40 cm, manufactured by Merck; eluent: methanol+0.1% diethylamine; flow rate: 200 ml/min).
MS: M+1=480
m.p.: tenacious resin

EXAMPLE 40 trans-8-(2-Aminocyclohexyloxy)-3-methyl-7-(3-methylbut-2-enyl)-1-(2-oxo-2-phenylethyl)-3,7-dihydropurine-2,6-dione hydrochloride (diastereomer 1)

This compound was obtained as the faster-eluting isomer by chromatographic separation of the mixture of diastereomers (Example 32) on a chiral column (Chiralpak AD 10×40 cm, manufactured by Merck; eluent: methanol+0.1% diethylamine; flow rate: 200 ml/min).
MS: M+1=466

EXAMPLE 41 trans-8-(2-Aminocyclohexyloxy)-3-methyl-7-(3-methylbut-2-enyl)-1-(2-oxo-2-phenylethyl)-3,7-dihydropurine-2,6-dione hydrochloride (diastereomer 2)

This compound was obtained as the isomer with the longer retention time by chromatographic separation of the mixture of diastereomers (Example 32) on a chiral column (Chiralpak AD 10×40 cm, manufactured by Merck; eluent: methanol+0.1% diethylamine; flow rate: 200 ml/min).
MS: M+1=466

EXAMPLE 42 trans-8-(2-Aminocyclohexyloxy)-7-(2-chlorobenzyl)-1,3-dimethyl-3,7-dihydropurine-2,6-dione

MS: M+1=418

The following examples illustrate the preparation of the starting materials:

EXAMPLE 43

8-Bromo-3-methyl-3,7-dihydropurine-2,6-dione 100 g of 3-methyl-3,7-dihydropurine-2,6-dione and 49 g of sodium acetate are suspended in 800 ml of glacial acetic acid and heated to an internal temperature of 90° C., and 33.3 ml of bromine are slowly (approx. 3-4 hours) added. The suspension is the stirred at this temperature for 3 hours when, according to TLC (DCM/MeOH 10:1), the reaction is complete. The reaction solution is cooled and filtered with suction. The residue is washed with 100 ml of glacial acetic acid and 500 ml of water and dried in vacuo at 50° C.

Yield: 145 g
m.p.: >300° C. (decomp.)

EXAMPLE 44

8-Bromo-3-methyl-7-(3-methylbut-2-enyl)-3,7-dihydropurine-2,6-dione 50 g of 8-bromo-3-methyl-3,7-dihydropurine-2,6-dione are introduced into 900 ml of DMF, and 14.1 g of potassium carbonate are added. The suspension is heated to an internal temperature of 60° C., and 31.7 g of 1-bromo-3-methyl-2-butene are slowly 10 added. The mixture is stirred at this temperature for 3 hours and then 1.2 l of water are added. The solid is filtered off with suction, thoroughly washed with water and dried in vacuo at 45° C.

Yield: 63.9 g
m.p.: 223.3° C.

EXAMPLE 45

8-Bromo-3-methyl-7-(3-methylbut-2-enyl)-1-(2-oxo-2-phenylethyl)-3,7-dihydropurine-2,6-dione 30 g of 8-bromo-3-methyl-7-(3-methylbut-2-enyl)-3,7-dihydropurine-2,6-dione, 20.6 g of phenacyl bromide and 25.4 g of potassium carbonate are introduced into 400 ml of DMF and heated at an internal temperature of 80° C. for 3 hours. The solution is cooled to about 50° C., and 400 ml of water are slowly added. The mixture is then stirred overnight, and precipitated solid is filtered off with suction. After washing the water, the pale brown solid is recrystallized from 300 ml of isopropanol.

Yield: 39.7 g
m.p.: 90.4° C.

What is claimed is:

1. A compound of the formula I

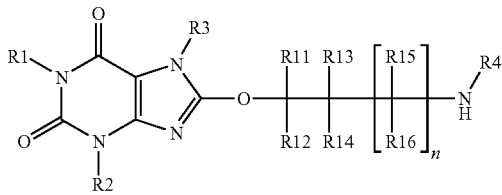

wherein:

R1, R2 and, R3 are independently selected from the group consisting of ($C_1$-$C_6$)-alkyl, ($C_3$-$C_{10}$)-cycloalkyl, ($C_2$-$C_{10}$)-alkenyl, ($C_2$-$C_{10}$)-alkynyl, ($C_6$-$C_{10}$)-aryl, and ($C_6$-$C_{10}$)-heterocycle, wherein the alkyl, cycloalkyl, alkenyl, alkynyl, aryl and heterocycle substituents may be replaced one or more times by F, Cl, Br, CN, $NO_2$, $SF_5$, OH, ($C_1$-$C_6$)-alkyl, —$CF_3$, —$OCF_3$, —$SCF_3$, ($C_2$-$C_6$)-alkenyl, ($C_2$-$C_6$)-alkynyl, OR7, NR7R8, NR7CONR7R8, COR7, COOR7, CONR7R8, ($C_1$-$C_6$)-alkylene-OR7, ($C_1$-$C_6$)-alkylene-NR7R8, ($C_1$-$C_6$)-alkylene-NR7$SO_2$R7, ($C_1$-$C_6$)-alkylene-SR7, alkylene-S(O)R7, alkylene -CONR7R8, SR7, SOR7, $SO_2$R7, $SO_2$NR7R8, NR7$SO_2$R7, ($C_1$-$C_6$)-alkylene-($C_3$-$C_{10}$)-cycloalkyl, ($C_1$-$C_6$)-alkylene-($C_6$-$C_{10}$)-aryl, ($C_1$-$C_6$)-alkylene-heterocycle, ($C_3$-$C_{10}$)-cycloalkyl, ($C_6$-$C_{10}$)-aryl or heterocycle; with the proviso that R1=R2=R3=methyl are excluded;

R7 and R8 are independently selected from the group consisting of H, ($C_1$-$C_6$)-alkyl, ($C_3$-$C_{10}$)-cycloalkyl, aryl, heterocycle ($C_1$-$C_4$)-alkylene-($C_6$-$C_{10}$)-aryl and ($C_1$-$C_4$)-alkylene-heterocycle;

R4 is hydrogen;

R11, R12, R13, R14, R15 and R16 are independently selected from the group consisting of H, ($C_1$-$C_6$)-alkyl or C3-C7-cycloalkyl, ($C_1$-$C_4$)-alkylene-aryl and ($C_1$-$C_4$)-alkylene-heterocycle; and n is 0;

or a pharmaceutically acceptable salt thereof.

2. A compound of formula I as recited in claim 1 wherein:

R1, R2 and, R3 are independently selected from the group consisting of ($C_1$-$C_6$)-alkyl, ($C_3$-$C_{10}$)-cycloalkyl, ($C_2$-$C_{10}$)-alkenyl, ($C_2$-$C_{10}$)-alkynyl, ($C_6$-$C_{10}$)-aryl, and heterocycle, where the alkyl, cycloalkyl, alkenyl, alkynyl, aryl and heterocycle substituents may be substituted one or more times by F, Cl, CN, $SF_5$, ($C_1$-$C_6$)-alkyl, —$CF_3$, —$OCF_3$, —$SCF_3$, ($C_2$-C4)-alkenyl, ($C_2$-C4)-alkynyl, OR7, NR7R8, NR7CONR7R8, COR7, COOR7, CONR7R8, ($C_1$-C4)-alkylene-OR7, ($C_1$-C4)-alkylene-NR7R8, ($C_1$-C4)-alkylene-NR7$SO_2$R7, ($C_1$-$C_6$)-alkylene-SR7, alkylene-S(O)R7, alkylene-CONR7R8, SR7, SOR7, $SO_2$R7, $SO_2$NR7R8, NR7$SO_2$R7, ($C_1$-$C_6$)-alkylene-($C_3$-$C_{10}$)-cycloalkyl, ($C_1$-$C_6$)-alkylene-($C_6$-$C_{10}$)-aryl, ($C_1$-$C_6$)-alkylene-heterocycle, ($C_3$-$C_{10}$)-cycloalkyl, ($C_6$-$C_{10}$)-aryl or heterocycle; with the proviso that R1=R2=R3=methyl are excluded;

R7 and R8 are independently selected from the group consisting of H, ($C_1$-$C_6$)-alkyl, ($C_3$-$C_{10}$)-cycloalkyl, aryl, heterocycle, ($C_1$-$C_4$)-alkylene-($C_6$-$C_{10}$)-aryl or ($C_1$-$C_4$)-alkylene-heterocycle;

R4 is hydrogen;

R11, R12, R13, R14 are independently selected from the group consisting of H, and ($C_1$-C4)-alkyl; and n is 0;

or a pharmaceutically acceptable salt thereof.

3. A pharmaceutical composition comprising a compound selected from the group consisting of those as recited in claim 1 in combination with at least one additional agent consisting of one or more excipients, bulking agents, fillers stabilizers, tableting agents, solvents, solubilizers and mixtures thereof.

4. A pharmaceutical composition comprising a compound selected from the group consisting of those as recited in claim 1 in combination with at least one additional agent consisting of one or more excipients, bulking agents, fillers stabilizers, tableting agents, solvents, solubilizers and mixtures thereof.

5. A pharmaceutical composition comprising a compound selected from the group consisting of those as recited in claim 1 and at least one other secondary pharmacologically active substance effective in the treatment of metabolic disturbances or disorders.

6. The pharmaceutical composition of claim 5, wherein the other secondary pharmacologically active substance is selected from the group consisting of one or more anti-diabetic agents, anti-hypoglycemic agents, HMGCoA reductase inhibitors, cholesterol absorption inhibitors, PPAR gamma agonists, PPAR alpha agonists, PPAR alpha/gamma agonists, fibrates, MTP inhibitors, bile acid absorption inhibitors, CETP inhibitors, polymeric bile acid adsorbents, LDL receptor inducers, ACAT inhibitors, antioxidants, lipoprotein lipase inhibitors, ATP-citrate lyase inhibitors, squalene synthetase inhibitors, lipoprotein(a) antagonists, lipase inhibitors, insulins, sulfonylureas, bisguanides, thiazolidinediones, α-glucosidase inhibitors, active ingredients which act on the ATP-dependent potassium channel of the beta cells, CART agonists, NPY agonists, CB-1 receptor antagonists, MCH antagonists, MC4 agonists, orexin agonists, TNF agonists, CRF agonists, CRF BP antagonists, urocortin agonists, βagonists, MSH (melanocyte-stimulating hormone) agonists, CCK agonists, serotonin reuptake inhibitors, mixed serotoninergic and noradrenergic compounds, 5HT agonists, bombesin agonists, galanin antagonists, growth hormones, growth hormone-releasing compounds, TRH agonists, uncoupling protein 2 or 3 modulators, leptin agonists, DA agonists, lipase/amylase inhibitors, PPAR modulators, RXR modulators, TR-βagonists, amphetamines and suitable mixtures thereof.

7. A process for the preparation of a pharmaceutical composition consisting of one or more of the compounds as recited in claim 1, wherein the compound as defined by formula I is mixed with a pharmaceutically suitable carrier comprising one or more excipients, bulking agents, fillers, stabilizers, tableting agents, solvents, solubilizers and mixtures thereof which is formulated suitable for administration to a patient in need thereof.

8. A composition for the treatment of elevated blood glucose levels and the diseases associated therewith consisting of the compound of formula I

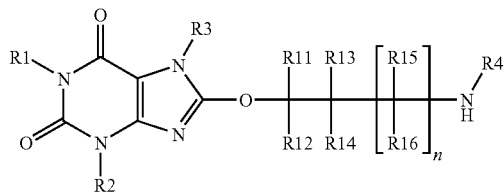

wherein:

R1, R2 and, R3 are independently selected from the group consisting of $(C_1-C_6)$-alkyl, $(C_3-C_{10})$-cycloalkyl, $(C_2-C_{10})$-alkenyl, $(C_2-C_{10})$-alkynyl, $(C_6-C_{10})$-aryl, and $(C_6-C_{10})$-heterocycle, wherein the alkyl, cycloalkyl, alkenyl, alkynyl, aryl and heterocycle substituents may be replaced one or more times by F, Cl, Br, CN, $NO_2$, $SF_5$, OH, $(C_1-C_6)$-alkyl, —$CF_3$, —$OCF_3$—$SCF_3$, $(C_2-C_6)$-alkenyl, $(C_2-C_6)$-alkynyl, OR7, NR7R8, NR7CONR7R8, COR7, COOR7, CONR7R8, $(C_1-C_6)$-alkylene-OR7, $(C_1-C_6)$-alkylene-NR7R8, $(C_1-C_6)$-alkylene-NR7SO$_2$R7, $(C_1-C_6)$-alkylene-SR7, alkylene-S(O)R7, alkylene-CONR7R8, SR7, SOR7, $SO_2$R7, $SO_2$NR7R8, NR7SO$_2$R7, $(C_1-C_6)$-alkylene-$(C_3-C_{10})$ cycoalkyl,$(C_1-C_6)$-alkylene-$(C_6-C_{10})$-aryl, $(C_1-C_6)$ alkylene-heterocycle, $(C_3-C_{10})$-cycloalkyl, $(C_6-C_{10})$-aryl or heterocycle; with the proviso that R1=R2=R3=methyl are excluded;

R7 and, R8 are independently selected from the group consisting of H, $(C_1-C_6)$-alkyl, $(C_3-C_{10})$ cycloalkyl, aryl, heterocycle, $(C_1-C_4)$-alkylene-$(C_6-C_{10})$-aryl and $(C_1-C_4)$-alkylene-heterocycle;

R4 is hydrogen;

R11, R12, R13, R14, R15 and R16 are independently selected from the group consisting of H, $(C_1-C_6)$-alkyl or C3-C7-cycloalkyl, $(C_1-C_4)$-alkylene-aryl and $(C_1-C_4)$-alklene-heterocycle; and n is 0 or 1;

with the further stipulation that the compound 1,3-di(cyclopropylmethyl)-7-(4-methoxybenzyl)-8-(4-piperidinyloxy)xanthine is excluded, and a pharmaceutically acceptable salt thereof in combination with a second active agent, wherein the second active ingredient is selected from the group consisting of one or more anti-diabetic agents, anti-hypoglycemic agents, HMGCoA reductase inhibitors, cholesterol absorption inhibitors, PPAR gamma agonists, PPAR alpha agonists, PPAR alpha/gamma agonists, fibrates, MTP inhibitors, bile acid absorption inhibitors, CETP inhibitors, polymeric bile acid adsorbents, LDL receptor inducers, ACAT inhibitors, antioxidants, lipoprotein lipase inhibitors, ATP-citrate lyase inhibitors, squalene synthetase inhibitors, lipoprotein(a) antagonists, lipase inhibitors, insulins, sulfonylureas, bisguanides, thiazolidinediones, α-glucosidase inhibitors, active ingredients which act on the ATP-dependent potassium channel of the beta cells, CART agonists, NPY agonists, CB-1 receptor antagonists, MCH antagonists, MC4 agonists, orexin agonists, TNF agonists, CRF agonists, CRF BP antagonists, urocortin agonists, β3 agonists, MSH (melanocyte-stimulating hormone) agonists, CCK agonists, serotonin reuptake inhibitors, mixed serotonergic and noradrenergic compounds, 5HT agonists, bombesin agonists, galanin antagonists, growth hormones, growth hormone-releasing compounds, TRH agonists, uncoupling protein 2 or 3 modulators, leptin agonists, DA agonists, lipase/amylase inhibitors, PPAR modulators, RXR modulators, TR-βagonists, amphetamines and suitable mixtures thereof.

* * * * *